US008158850B2

(12) United States Patent
Feng et al.

(10) Patent No.: US 8,158,850 B2
(45) Date of Patent: Apr. 17, 2012

(54) METHOD TO ENHANCE YIELD AND PURITY OF HYBRID CROPS

(75) Inventors: Paul C. C. Feng, Wildwood, MO (US); Oscar Heredia, High Hill, MO (US); Arnold A. Rosielle, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 268 days.

(21) Appl. No.: 12/338,897

(22) Filed: Dec. 18, 2008

(65) Prior Publication Data
US 2009/0165166 A1    Jun. 25, 2009

Related U.S. Application Data

(60) Provisional application No. 61/015,102, filed on Dec. 19, 2007, provisional application No. 61/074,963, filed on Jun. 23, 2008.

(51) Int. Cl.
*A01H 1/00* (2006.01)
(52) U.S. Cl. .................................. 800/272; 800/275
(58) Field of Classification Search ................... None
See application file for complete search history.

(56) References Cited

U.S. PATENT DOCUMENTS

| | | | |
|---|---|---|---|
| 4,735,649 A | 4/1988 | Dhingra et al. | |
| 4,940,835 A | 7/1990 | Shah et al. | |
| 4,971,908 A | 11/1990 | Kishore et al. | |
| 5,094,945 A | 3/1992 | Comai | 435/172.3 |
| 5,145,783 A | 9/1992 | Kishore et al. | |
| 5,188,642 A | 2/1993 | Shah et al. | |
| 5,356,799 A | 10/1994 | Fabijanski et al. | |
| 5,463,175 A | 10/1995 | Barry et al. | 800/205 |
| 5,489,520 A | 2/1996 | Adams et al. | |
| 5,554,798 A | 9/1996 | Lundquist et al. | |
| 5,627,061 A | 5/1997 | Barry et al. | 435/172.3 |
| 5,633,435 A | 5/1997 | Barry et al. | 800/205 |
| 5,633,441 A | 5/1997 | De Greef et al. | 800/205 |
| 5,750,868 A | 5/1998 | Cigan et al. | 800/205 |
| 6,040,497 A | 3/2000 | Spencer et al. | 800/288 |
| 6,046,382 A | 4/2000 | Mariani et al. | 800/274 |
| 6,057,496 A | 5/2000 | Conner | |
| 6,255,564 B1 | 7/2001 | Fabijanski et al. | 800/286 |
| 6,338,961 B1 | 1/2002 | Derose et al. | |
| 6,384,304 B1 | 5/2002 | Quandt et al. | 800/320.3 |
| 6,476,291 B1 | 11/2002 | Conner | |
| 6,566,587 B1 | 5/2003 | Lebrun et al. | |
| 6,646,186 B1 | 11/2003 | Stine et al. | 800/312 |
| 6,750,377 B1 | 6/2004 | Kaster, Jr. et al. | |
| 6,762,344 B1 | 7/2004 | Spencer et al. | 800/320.1 |
| 7,314,970 B2 | 1/2008 | Spencer et al. | 800/300 |
| 7,405,347 B2 | 7/2008 | Hammer et al. | 800/300 |
| 2003/0083480 A1 | 5/2003 | Castle et al. | 800/300 |
| 2005/0086719 A1 | 4/2005 | Spencer et al. | |
| 2005/0150013 A1 | 7/2005 | Hawkes et al. | 800/274 |
| 2006/0015968 A1 | 1/2006 | Albertsen et al. | 536/23.6 |
| 2006/0059581 A1 | 3/2006 | Spencer et al. | 800/300 |
| 2006/0143727 A1 | 6/2006 | Alibhai et al. | 800/300 |
| 2006/0200874 A1 | 9/2006 | Castle et al. | 800/300 |
| 2007/0197474 A1 | 8/2007 | Clinton et al. | |

FOREIGN PATENT DOCUMENTS

| | | |
|---|---|---|
| EP | 0 242 236 A1 | 10/1987 |
| EP | 0 737 749 A1 | 10/1996 |
| EP | 0 426 641 B1 | 9/2000 |
| EP | 0 329 308 B1 | 10/2001 |
| WO | WO 90/08828 A2 | 8/1990 |
| WO | WO 92/00377 | 1/1992 |
| WO | WO 92/04454 A1 | 3/1992 |
| WO | WO 95/06128 A2 | 3/1995 |
| WO | WO 96/40950 A1 | 12/1996 |
| WO | WO 97/04103 A2 | 2/1997 |
| WO | WO 97/04114 A2 | 2/1997 |
| WO | WO 97/23634 A2 | 7/1997 |
| WO | WO 98/39419 | 9/1998 |
| WO | WO 98/44140 | * 10/1998 |
| WO | WO 02/071834 | 9/2002 |
| WO | WO 2004/009761 | 1/2004 |
| WO | WO 2005/003362 | 1/2005 |
| WO | WO 2005/102057 | 11/2005 |
| WO | WO 2006/110586 | 10/2006 |

OTHER PUBLICATIONS

Mariani et al., "A chimaeric ribonuclease-inhibitor gene restors fertility to male sterile plants," *Nature*, 357:384-387, 1992.
Armstrong et al., "Field evaluation of European corn borer control in progeny of 173 transgenic corn events expressing an insecticidal protein from *Bacillus thuringiensis*," *Crop Sci.*, 35:550-557, 1995.
Frascaroli et al., "Variability of pollen and plant responses to glyphosate in maize," *J. Genet. & Breed.*, 46:49-56, 1992.
Hansen et al., "Recent advances in the transformation of plants," *Trends in Plant Sci*, 4(6):226-231, 1999.
Howe et al., "Development of glyphosate as a selectable marker for the production of fertile transgenic corn plants," *In Vitro Cell. & Devel. Biol.*, 28(3):124A, 1992.
Mariani et al., "The production and analysis of genetically engineered male-sterile plants of maize," *In Vitro Cell. & Devel. Biol.*, 28(3), Part II, 1992. Oommenn et al., "The elicitor-inducible alfalpha isoflavone reductase promoter confers different patterns of developmental expression in homologous and heterologous transgenic plants," *The Plant Cell*, 6:1789-1803, 1994.
Padgette et al., "New weed control opportunities: development of soybeans with Roundup Ready™ gene," In: Herbicide Resistant Crops, Padgette et al. (Eds.), CRC Press Inc., pp. 53-84, London, UK, 1996.
Spencer et al., "Segregation of transgenes in maize," *Plant Mol. Biol.*, 18(2):201-210, 1992.
Wit, "Chemically induced male sterility, a new tool in plant breeding?," *Euphy*, May 1960 9(1): 1-9.

* cited by examiner

*Primary Examiner* — David H Kruse
(74) *Attorney, Agent, or Firm* — SNR Denton US LLP; Pamela Sisson

(57) ABSTRACT

The present invention provides a method of herbicide treatment of selected female and male parents in a hybrid seed production system. The system results in enhanced trait purity and efficiency in the hybrid seed production system.

17 Claims, 1 Drawing Sheet

SEQUENCE LISTING

<160> NUMBER OF SEQ ID NOS: 10

<210> SEQ ID NO 1
<211> LENGTH: 27
<212> TYPE: DNA
<213> ORGANISM: artificial
<220> FEATURE:
<223> OTHER INFORMATION: synthetic sequence

<400> SEQUENCE: 1
atgaatgacc tcgagtaagc ttgttaa                                27

<210> SEQ ID NO 2
<211> LENGTH: 28
<212> TYPE: DNA
<213> ORGANISM: artificial
<220> FEATURE:
<223> OTHER INFORMATION: synthetic sequence

<400> SEQUENCE: 2
aagagataac aggatccact caaacact                               28

<210> SEQ ID NO 3
<211> LENGTH: 26
<212> TYPE: DNA
<213> ORGANISM: artificial
<220> FEATURE:
<223> OTHER INFORMATION: synthetic sequence

<400> SEQUENCE: 3
tggtaccacg cgacacactt ccactc                                 26

<210> SEQ ID NO 4
<211> LENGTH: 20
<212> TYPE: DNA
<213> ORGANISM: artificial
<220> FEATURE:
<223> OTHER INFORMATION: synthetic sequence

<400> SEQUENCE: 4
agccaccact tctccttgga                                        20

<210> SEQ ID NO 5
<211> LENGTH: 21
<212> TYPE: DNA
<213> ORGANISM: artificial
<220> FEATURE:
<223> OTHER INFORMATION: synthetic sequence

<400> SEQUENCE: 5
aggctaccga aagtcctcgt t                                      21

<210> SEQ ID NO 6
<211> LENGTH: 23
<212> TYPE: DNA
<213> ORGANISM: artificial
<220> FEATURE:
<223> OTHER INFORMATION: synthetic sequence

<400> SEQUENCE: 6
atcgatgtgg gctgcaccga cct                                    23

<210> SEQ ID NO 7
<211> LENGTH: 22
<212> TYPE: DNA

```
<213> ORGANISM: artificial
<220> FEATURE:
<223> OTHER INFORMATION: synthetic sequence

<400> SEQUENCE: 7
gcttgatggg gatcagattg tc                                              22

<210> SEQ ID NO 8
<211> LENGTH: 17
<212> TYPE: DNA
<213> ORGANISM: artificial
<220> FEATURE:
<223> OTHER INFORMATION: synthetic sequence

<400> SEQUENCE: 8
cgtttcccgc cttcagt                                                    17

<210> SEQ ID NO 9
<211> LENGTH: 19
<212> TYPE: DNA
<213> ORGANISM: artificial
<220> FEATURE:
<223> OTHER INFORMATION: synthetic sequence

<400> SEQUENCE: 9
gcagtatgcc ggagttgac                                                  19

<210> SEQ ID NO 10
<211> LENGTH: 17
<212> TYPE: DNA
<213> ORGANISM: artificial
<220> FEATURE:
<223> OTHER INFORMATION: synthetic sequence

<400> SEQUENCE: 10
catccaaacc cgactct                                                    17
```

US 8,158,850 B2

METHOD TO ENHANCE YIELD AND PURITY OF HYBRID CROPS

This application claims the priority of U.S. Provisional Applications Ser. Nos. 61/015,102 and 61/074,963, filed Dec. 19, 2007 and Jun. 23, 2008, respectively, the entire disclosures of which are incorporated herein by reference.

BACKGROUND OF THE INVENTION

Incorporation-by-Reference of Sequence Listing in Computer Readable Form

The Sequence Listing, which is a part of the present disclosure, includes a computer readable form 2.39 kb file entitled "MONS181US_SEQ.txt" comprising nucleotide sequences of the present invention submitted via EFS-Web. The subject matter of the Sequence Listing is incorporated herein by reference in its entirety.

FIELD OF THE INVENTION

The present invention relates generally to methods for producing hybrid seed. More specifically, it relates to methods that provide an inducible male sterile plant and a hybrid seed production system that results in enhanced yield, trait purity, and reduced costs relative to other known methods of producing hybrid seed.

DESCRIPTION OF RELATED ART

Commercial hybrid seed production, such as hybrid corn (maize, Zea mays) seed production, is an expensive and labor intensive process. Single cross hybrid corn seed production involves the production of male and female parent lines, and planting these in separate rows or blocks in an isolated field. The female parent must be treated to prevent pollen shed (e.g. manual or mechanical detasseling) to ensure only pollination by the male parent. The male parents must be destroyed following pollination to prevent seed mixing during harvest usually be a mechanical means. Ears from the cross-pollinated female parent are harvested, processed, and the seed sold to farmers for planting as hybrid seed. The detasseling period is usually the most critical and difficult to manage period in hybrid corn seed production. Other costs include specialized equipment, fuel, herbicides, and fungicides. Reducing these costs while maintaining a high level of hybrid seed purity is key to profitability in hybrid corn seed production. A high level of hybrid seed purity results in higher yield of corn crop planted with the hybrid seed.

Many methods have been developed to replace mechanical and hand detasseling in corn hybrid seed production. These include cytoplasmic male sterility (CMS). However, the CMS trait in the hybrid plants is sometimes associated with reduced agronomic performance and susceptibility to certain crop diseases. This problem and the need to maintain inventory of various CMS varieties has led to the reduction in the use CMS in producing hybrid corn. In addition, CMS sometimes has a negative association with stalk quality, early seedling vigor, and yield. CMS may show a breakdown of sterility in certain environments, rendering CMS lines unreliable for hybrid seed production. The failure of CMS in a hybrid production field may result in a complete loss of the hybrid seed crop.

There is a need for an effective hybrid production system, and methods for inducing male sterility in corn have been developed through biotechnology. The SeedLink™ system uses an RNase nuclear gene called barnase and a glufosinate-tolerance gene (e.g. Mariani et al., Nature 357:384-387, 1992). U.S. Patent Application Publication 20060015968 uses an isolated corn male-sterile gene and a chemically-inducible promoter. A chemical restorer system has been developed (WO02071834) requiring the expression of a biotin binding protein in pollen that causes male sterility. Fertility can be restored by the addition of biotin. A hybrid seed system was also developed in which a cytotoxic product is expressed that disrupts pollen formation (U.S. Pat. No. 5,750,868). Spencer (U.S. Pat. No. 6,762,344) developed a simple corn hybrid system based on differential sensitivity of pollen producing cells to glyphosate (n-phosphonomethylglycine).

The present invention provides a new method that optimizes the glyphosate gametocide effect in a corn hybrid production field and provides the unexpected results of enhanced hybrid purity, enhanced transgenic trait purity, and enhanced yield of the hybrid seed. This method is useful for increasing broad acre yield of the hybrid corn crop. Additional benefits of glyphosate treatment, such as weed control in the production field, herbicide replacement, and disease control are within the scope of the invention. The present invention additionally provides a method applicable to any plant in which a hybrid seed production system is desired by providing a selective system to induce male sterility in a female parent by application of a first herbicide, then selectively removing the pollen producing plants after pollination by treatment with an application of a second herbicide for which the female parent is tolerant.

SUMMARY OF THE INVENTION

Figure 1:
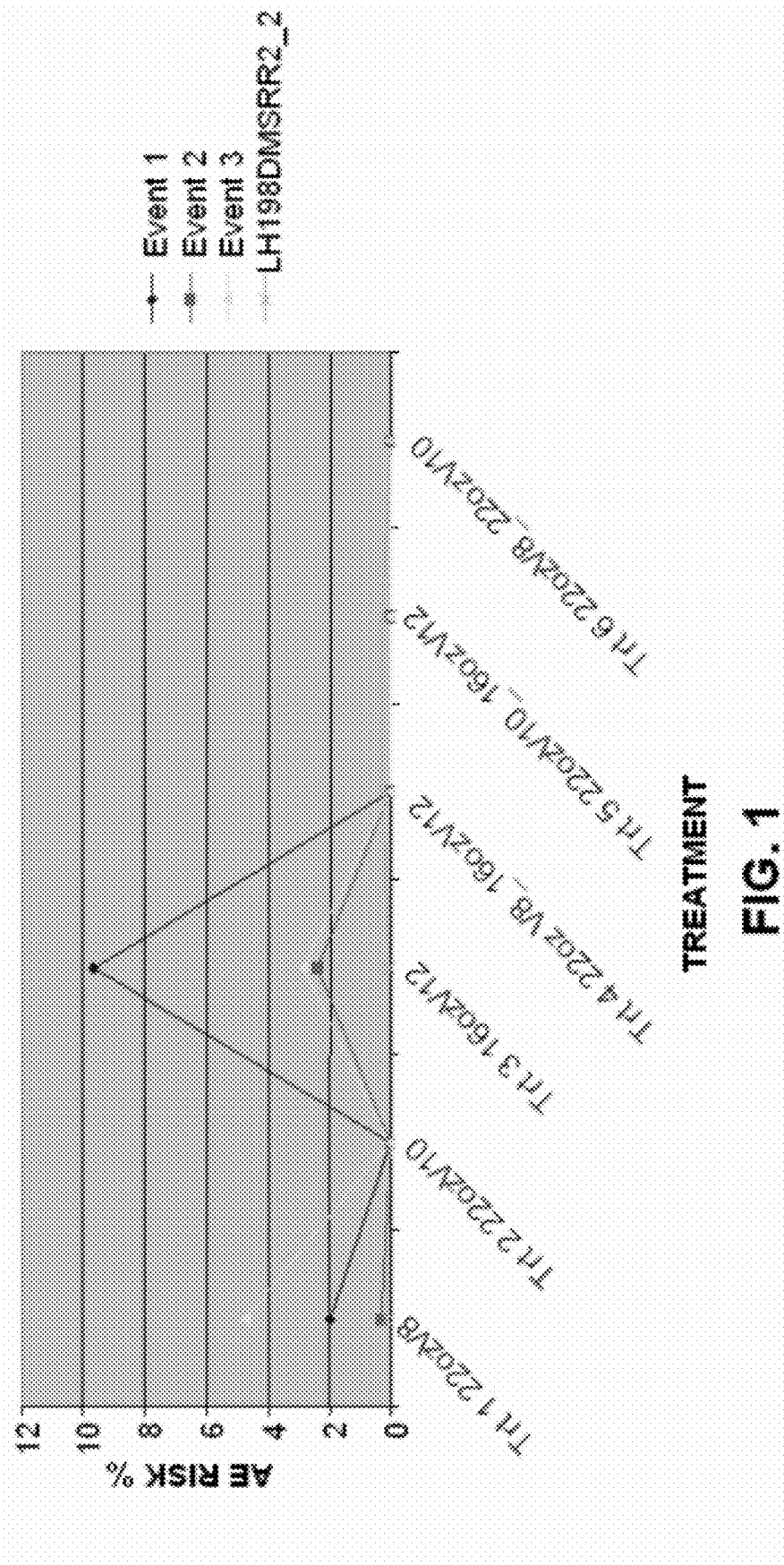
FIG. 1: Glyphosate treatment of selected transgenic corn events measuring the response in percent anther extrusion (AE) with varying doses of glyphosate.

In one aspect, the invention relates to a method for corn hybrid seed single cross or modified single cross production that enhances transgene trait purity, genotype purity, or hybrid seed yield, or reduces the cost of hybrid seed production, comprising: (a) planting in a hybrid corn seed production field in pollinating proximity, seeds of a first parent corn plant and a second parent corn plant; (b) allowing said seeds to germinate and grow into plants, wherein said first parent corn plant comprises a first glyphosate tolerance transgene and is homozygous for said first glyphosate tolerance transgene and said second parent corn plant comprises a second glyphosate tolerance transgene and is homozygous for said second glyphosate tolerance transgene; (c) treating said plants in said seed production field with at least one treatment of glyphosate, wherein said treatment consists of: (i) a single application of glyphosate of about 0.54 ae/ac or more at about the V8 growth stage or later; or (ii) two applications of glyphosate of about 0.54-0.75 ae/ac at about the V8-V12 growth stages; and wherein said first parent corn plant is vegetatively and female reproductively tolerant to said glyphosate treatment and rendered male-sterile by said glyphosate treatment, and wherein said second parent corn plant is vegetatively, female, and male reproductively tolerant to said glyphosate treatment; (d) allowing the second corn parent plants to pollinate the first parent corn plants in said production field; and (e) harvesting a hybrid corn seed produced on the first parent corn plant in said production field.

In particular embodiments, step (c) comprises: treating said plants in said seed production field with at least one treatment of glyphosate, wherein said treatment consists of: (i) about 0.75 lb ae/ac or more applied at the V10 growth stage; or (ii) about 0.75 lb ae/ac or more applied at the V8 stage followed by about 0.54 lb ae/ac or more applied at the V12 growth stage; or (iii) about 0.75 lb ae/ac or more applied at the V10 stage followed by about 0.54 lb ae/ac or more applied at the V12 growth stage; or (iv) about 0.75 lb ae/ac or more applied at the V8 stage followed by about 0.75 lb ae/ac or more applied at the V10 growth stage; and wherein said first parent corn plant is vegetatively and female reproductively tolerant to said glyphosate treatment and rendered male-sterile by said glyphosate treatment, and wherein said second parent corn plant is vegetatively, female and male reproductively tolerant to said glyphosate treatment.

In certain embodiments the method enhances transgene trait purity and genotype purity. In another embodiment the method enhances hybrid seed yield, relative to the hybrid seed yield of a hybrid corn seed production field comprising the same parental genotypes, but not grown under the method described herein. In particular embodiments, hybrid seed yield is enhanced by 2%, 3%, 5%, 10%, 15%, or 20%. In yet another embodiment, the method reduces the cost of hybrid seed production.

In certain embodiments of the invention, a sample of the hybrid seed can additionally be assayed with a first molecular marker specific for the first glyphosate tolerance transgene and a second molecular marker specific for the second glyphosate tolerance transgene, wherein the transgene trait purity and genotype purity of said hybrid seed produced by said hybrid seed production system is greater than in a hybrid seed production field not using said method of hybrid seed production.

In another embodiment of the invention, the female plants are not mechanically detasseled or hand detasseled, and labor costs are reduced.

In yet other embodiments of the invention, the costs of treatment with a non-glyphosate herbicide are reduced, there is a reduced cost due to reduced risk of injury to production workers, a fuel cost is reduced, a cost of fungicide application is reduced, a cost of equipment is reduced, and CMS germplasm is not used. In particular embodiments, one or more of these costs, or the total of these costs, are reduced by 1%, 2%, 3%, 4%, 5%, 8%, 10%, or 15% relative to the costs incurred in producing hybrid corn seed not using the hybrid seed production method.

The invention further relates to hybrid corn seed produced by the single cross or modified single cross method of the present invention, said seed comprising within its genome a first T-DNA comprising at least one transgene derived from the first parent, and a second T-DNA comprising at least one transgene derived from the second parent; wherein said first and second T-DNAs comprise a glyphosate tolerance transgene. The T-DNA molecules of each parent can be assayed by a molecular marker molecular specific for each T-DNA. In certain embodiments, markers are used to assay a sample of the hybrid seed and confirm that the transgene trait purity of the sample is at least 98% with respect to the assayed marker; that is the desired trait(s) occur in at least ninety-eight percent of the sample assayed. The first and second T-DNAs may additionally comprise a second transgene that confers an agronomically useful trait. The second transgene comprises a trait selected from the group consisting of insect resistance, enhanced yield, herbicide tolerance, disease resistance, an enhanced processing trait, stress tolerance, and any combination thereof. In certain embodiments, the corn seed additionally comprises within its genome a molecular marker specific for the first parent and the second parent genotype. The markers are used to assay a sample of the hybrid seed and to confirm that the genotype purity of the sample is at least 98%; that is, the desired trait(s) occur in at least ninety-eight percent of the sample assayed.

The hybrid corn seed produced by the method of the present invention comprises a high level of transgene trait purity and genotype purity that results in higher yield of a corn crop planted with the hybrid seed than the yield of a corn crop planted with a hybrid seed of the same genotype not produced by the method.

In another aspect, the invention relates to a method for producing hybrid corn seed by a multi-cross production system that enhances transgene trait purity and genotype purity comprising: (a) planting in a hybrid corn seed production field in pollinating proximity, seeds of a first parent corn plant that is a homozygous inbred or a hybrid and a second parent corn plant is a hybrid or open pollinated variety; (b) allowing said seeds to germinate and grow into plants, wherein said first parent corn plant comprises a first glyphosate tolerance transgene and said second parent corn plant comprises a second glyphosate tolerance transgene; (c) treating said plants in said seed production field with at least one treatment of glyphosate, wherein said treatment consists of: (i) a single application of glyphosate of about 0.54 ae/ac or more at about the V8 growth stage or later; or (ii) two applications of glyphosate of about 0.54-0.75 ae/ac at about the V8-V12 growth stages; and wherein said first parent corn plant is vegetatively and female reproductively tolerant to said glyphosate treatment and rendered male-sterile by said glyphosate treatment, and wherein said second parent corn plant is vegetatively, female, and male reproductively tolerant to said glyphosate treatment; (d) allowing the second corn parent plants to pollinate the first parent corn plants in said production field; and (e) harvesting a hybrid corn seed produced on the first parent corn plant in said production field.

In particular embodiments, step (c) comprises: (c) treating said plants in said seed production field with at least one treatment of glyphosate, wherein said treatment consists of: (i) about 0.75 lb ae/ac or more applied at the V10 growth stage; or (ii) about 0.75 lb ae/ac or more applied at the V8 stage followed by about 0.54 lb ae/ac or more applied at the V12 growth stage; or (iii) about 0.75 lb ae/ac or more applied at the V10 stage followed by about 0.54 lb ae/ac or more applied at the V12 growth stage; or (iv) about 0.75 lb ae/ac or more applied at the V8 stage followed by about 0.75 lb ae/ac or more applied at the V10 growth stage; and wherein said first parent corn plant is vegetatively and female reproductively tolerant to said glyphosate treatment and rendered male-sterile by said glyphosate treatment, and wherein said second parent corn plant is vegetatively, female and male reproductively tolerant to said glyphosate treatment.

In certain embodiments, a sample of the multi-cross hybrid seed is assayed with a first molecular marker specific for the first glyphosate tolerance transgene and a second molecular marker specific for the second glyphosate tolerance transgene, wherein the transgene trait purity and genotype purity of said hybrid seed produced by said hybrid seed production system is greater than that produced from a hybrid seed production field not using said hybrid seed production system.

In another aspect of the invention a method is provided for hybrid seed production comprising the steps of growing a first plant and a second plant in pollination proximity, wherein the first plant is capable of tolerating a first herbicide in the vegetative tissue and female reproductive tissue but not in the male reproductive tissue, and is capable of tolerating a second herbicide, and further wherein the second plant is capable of tolerating the first herbicide, and is sensitive to the second herbicide; treating the first and second plants, prior to pollination, with an effective amount of the first herbicide to render the first plant male sterile while allow pollen from the second plant to pollinate the first plant; treating the first and second plants, post pollination, with an effective amount of the second herbicide to halt the further development of the second plant; and harvesting seeds from the first plant.

In this method the first herbicide is a systemic herbicide, such as glyphosate, and the second herbicide is selected from the group consisting of dinitroaniline herbicide, trifluralin, pendimethalin, ethalfluralin, triazolopyrimidines, chloracetamide, metolachlor, acetochlor, dimethenamid-P, alachlor, thiocarbamate, triallate, EPTC, cycloate, benzolfuran, ethofumesate, pyrazolium, difenzoquat-methyl sulfate, a uracil, a phenylurea, a triketone, mesotrione, an isoxazole, isoxaflutole, an acetanilide, an oxadiazole, a triazinone, a sulfonanilide, an amide, an anilide, propanil, a flurochloridone, a norflurazon, a triazine, atrazine, a triazolinone type herbicide, metribuzin, flucarbazone-Na, propoxycarbazone-Na, glufosinate, asulam, bentazon, bialaphos, bromacil, sethoxydim, cyclohexanedione, tralkoxydim, clethodim, sethoxydim, phenylpyrazolin, pinoxaden, dicamba, fosarnine, flupoxam, 2-phenoxypropionate, aryloxy-phenoxypropionate, clodinafop-propargyl, fenoxaprop-P-ethyl, diclofop-methyl, fluazifop-P-butyl, quizalofop, picloram, fluormetron, butafenacil, metribuzin, chlorimuron, chlorsulfuron, triasulfuron, mesosulfuron-methyl, foramsulfuron, sulfosulfuron, flumetsulam, halosulfuron, sulfometron, imazamethabenz-methyl, imazaquin, imazethapyr, isoxaben, imazamox, metosulam, pyrithrobac, rimsulfuron, bensulfuron, nicosulfuron, fomesafen, fluroglycofen, KIEI9201, ET751, carfentrazone, mesotrione, sulcotrione, bypyridilium, paraquat, diquat, bromoxynil and fenoxaprop.

In another aspect, the method for hybrid seed production may be performed with a plant other than a corn plant. In certain embodiments the method for hybrid seed production may be performed with a plant selected from the group consisting of canola (*Brassica napus, Brassica rapa* ssp.), alfalfa (*Medicago sativa*), rice (*Oryza sativa*), rape (*Brassica napus*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batata*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus* sp.), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), oats, barley, ornamentals, conifers, and turfgrasses (ornamental, recreational or forage), vegetables such as tomato (*Lycopersicon esculentum*), lettuce (*Lactuca sativa*), carrots (*Daucus carota*), cauliflower (*Brassica oleracea*), celery (*Apium graveolens*), eggplant (*Solanum melongena*), asparagus (*Asparagus officinalis*), okra (*Abelmoschus esculentus*), green beans (*Phaseolus vulgaris*), lima beans (*Phaseolus limensis*), peas (*Pisum sativum, Lathyrus* spp.), *Cucurbita* species such as Hubbard squash (*C. maxima*), Butternut squash (*C. moschata*), zucchini (*C. pepo*), Crookneck squash (*C. melopepo*), *C. argyrosperma*, *C. argyrosperma* ssp *sororia*, *C. digitata*, *C. ecuadorensis*, *C. foetidissima*, *C. lundelliana*, and *C. martinezii*, *Cucumis* species such as cucumber (*Cucumis sativus*), cantaloupe (*C. cantalupensis*), and musk melon (*C. melo*).

Thus, in one aspect the invention comprises a method for hybrid seed production comprising the steps of: a) growing a first plant and a second plant in pollination proximity in a field, wherein the first plant is capable of tolerating a first herbicide in the vegetative tissue and female reproductive tissue but not in the male reproductive tissue, and is capable of tolerating a second herbicide, and further wherein the second plant is capable of tolerating the first herbicide, and is sensitive to the second herbicide; b) treating the first and second plants, prior to pollination, with an effective amount of the first herbicide to render the first plant male sterile while allowing pollen from the second plant to pollinate the first plant; c) treating the first and second plants, post pollination, with an effective amount of the second herbicide to halt the further development of the second plant; and d) harvesting seeds from the first plant.

In certain embodiments, the first herbicide is selected from the group consisting of glyphosate, an imidazolinone, a sulfonylurea, a sulfonamide, an aryloxyphenoxypropionate, and a cyclohexanedione. Likewise, in other embodiments, the second herbicide is selected from the group consisting of a dinitroaniline herbicide, trifluralin, pendimethalin, ethalfluralin, triazolopyrimidines, chloracetamide, metolachlor, acetochor, dimethenamid-P, alachlor, thiocarbamate, triallate, EPTC, cycloate, benzolfuran, ethofumesate, pyrazolium, difenzoquat-methyl sulfate, a uracil, a phenylurea, a triketone, mesotrione, an isoxazole, isoxaflutole, an acetanilide, an oxadiazole, a triazinone, a sulfonanilide, an amide, an anilide, propanil, a flurochloridone, a norflurazon, a triazine, atrazine, a triazolinone type herbicide, metribuzin, flucarbazone-Na, propoxycarbazone-Na, glufosinate, asulam, bentazon, bialaphos, bromacil, cyclohexanedione, tralkoxydim, clethodim, sethoxydim, phenylpyrazolin, pinoxaden, dicamba, fosarnine, flupoxam, 2-phenoxypropionate, aryloxy-phenoxypropionate, clodinafop-propargyl, fenoxaprop-P-ethyl, diclofop-methyl, fluazifop-P-butyl, quizalofop, picloram, fluormetron, butafenacil, metribuzin, chlorimuron, chlorsulfuron, triasulfuron, mesosulfuron-methyl, foramsulfuron, sulfosulfuron, flumetsulam, halosulfuron, sulfometron, imazamethabenz-methyl, imazaquin, imazethapyr, isoxaben, imazamox, metosulam, pyrithrobac, rimsulfuron, bensulfuron, nicosulfuron, fomesafen, fluroglycofen, KIEI9201, ET751, carfentrazone, mesotrione, sulcotrione, bypyridilium, paraquat, diquat, bromoxynil and fenoxaprop.

In certain embodiments the first herbicide tolerance is provided to the female parent and male parent plants by differential expression of a transgene comprising a glyphosate tolerant EPSPS, or a glyphosate inactivating enzyme. In some embodiments, the second herbicide tolerance is provided to the female parent plant by a transgene expressing a herbicide tolerance protein selected from the group consisting dicamba monooxygenase conferring tolerance to auxin-like herbicides such as dicamba, phosphinothricin acetyltransferase conferring tolerance to phosphinothricin or glufosinate, 2,2-dichloropropionic acid dehalogenase conferring tolerance to 2,2-dichloropropionic acid (Dalapon), acetohydroxyacid synthase or acetolactate synthase conferring tolerance to acetolactate synthase inhibitors such as sulfonylurea, imidazolinone, triazolopyrimidine, pyrimidyloxybenzoates and phthalide, haloarylnitrilase for conferring tolerance to bromoxynil, modified acetyl-coenzyme A carboxylase for conferring tolerance to cyclohexanedione (sethoxydim) and aryloxyphenoxypropionate (haloxyfop), dihydropteroate synthase for conferring tolerance to sulfonamide herbicides, 32 kD photosystem II polypeptide for conferring tolerance to triazine herbicides, anthranilate synthase for conferring tolerance to 5-methyltryptophan, dihydrodipicolinic acid synthase for conferring to tolerance to aminoethyl cysteine, phytoene desaturase for conferring tolerance to pyridazinone herbicides such as norflurazon, hydroxy-phenyl pyruvate dioxygenase for conferring tolerance to cyclopropylisoxazole herbicides such as isoxaflutole, modified protoporphyrinogen oxidase I for conferring tolerance to protoporphyrinogen oxidase inhibitors, and aryloxyalkanoate dioxygenase for conferring tolerance to an herbicide containing an aryloxyalkanoate moiety, phenoxy auxins (such as 2,4-D and dichlorprop), pyridyloxy auxins (such as fluroxypyr and triclopyr), aryloxyphenoxypropionates (AOPP) acetyl-coenzyme A carboxylase inhibitors (such as haloxyfop, quizalofop, and diclofop), and 5-substituted phenoxyacetate protoporphyrinogen oxidase IX inhibitors (such as pyraflufen and flumiclorac). A hybrid seed produced by a described method is also an aspect of the invention. In certain embodiments, the hybrid seed is a corn seed.

BRIEF DESCRIPTION OF THE INVENTION

Transgenic traits are expensive to develop and provide unique agronomically useful phenotypes to the crop plant that is unmet by conventional breeding methods. Often a trait fee is applied to the sale of the seed that provides for the cost of development of the trait and to fund future crop improvement technologies. In order to achieve the greatest value from the transgenic trait, a high percentage of the hybrid seed should have the trait. The present invention provides a method to enhance the presence of the trait in the hybrid seed. The present invention provides an enhanced method for hybrid seed production, referred to herein as the glyphosate hybridization system (GHS).

The method includes preferred timing and rates of application of a glyphosate herbicide to induce male-sterility in a differential glyphosate tolerant parent (i.e. possessing a genotype distinct from that of a first glyphosate tolerant plant) of a corn hybrid seed production field. The method provides for enhanced trait and genotype purity. The method provides for enhanced yield of the hybrid seed relative to conventional methods used to create hybrid seed. The method eliminates the need for expensive labor intensive and potentially dangerous mechanical and manual detasseling of the corn plants. The method allows for a field-wide application of a glyphosate treatment without the need to shield the male parent from the treatment. The method saves equipment and fuel costs and extends the time window in which sterility can be achieved over methods that use mechanical and manual detasseling. The method additionally provides a level of weed control in the field by application of an effective dose of glyphosate to control weeds growing in the field, thereby reducing the use of other, non-glyphosate, herbicides and saving the expense of these herbicides, the expense of application, and worker safety hazards associated with the non-glyphosate herbicides. Glyphosate has also been recently shown to have fungicidal effects when applied to glyphosate tolerant plants (WO05102057). The method thus also allows for a reduction in the use of fungicide compounds on the plants in the hybrid production field and reduces worker exposure to these fungicides. The method additionally incorporates a second herbicide tolerance transgene.

A hybrid corn seed is produced in a seed production system and terms that relate to hybrid seed production include, but are not limited to any of the following:

1. A single cross, such as, a first generation cross between two inbred lines.
2. A modified single cross, such as, a first generation cross between two inbred lines, one or other of which may have been modified slightly by the use of closely related crossing.
3. A double cross, such as, a first generation of a cross between two single crosses.
4. A three-way cross, such as, a first generation of a cross between a single cross and an inbred line.
5. A top cross, such as, the first generation of a cross between an inbred line and an open-pollinated variety, or the first generation of a cross between a single-cross and an open-pollinated variety.
6. Open pollinated variety, such as, a population of plants selected to a standard which may show variation but has characteristics by which a variety can be differentiated from other varieties.

The method additionally provides for enhanced transgene trait purity, genotype purity and yield of the hybrid seed. This permits higher yield of the crop planted with the hybrid seed produced by the method of the present invention. The higher yield is a result of enhanced trait purity and genotype purity. Hybrids of single crosses (with two inbred parental lines, the genotypes) are costly to produce. In corn, the parental lines suffer from an inbreeding depression resulting in lower yields of the seed line. Consequently, large areas must be utilized in order to generate the necessary quantity of hybrid seed, typically making seed production expensive. The advantage of single cross hybrids is that the yield is often about three times more seed per plant compared to the inbred parents. A high percentage of the seed produced in a hybrid production system should contain the genotypes of both parents.

CMS is a maternally inherited sterility trait that suppresses the production of viable pollen grains, typically through pollen abortion and, in some cases, by failure to extrude anthers. Restoration of fertility is under the control of nuclear gene(s), called restorer of fertility (Rf) that suppress the sterility but do not change the maternally inherited cytoplasm. Three major categories of CMS exist in corn: CMS-C (Charrua), CMS-T (Texas), and CMS-S (USDA). The genetic defect in CMS strains is due to the mitochondrial DNA (mtDNA). As such these different cytoplasms, normal (fertile), CMS-C, CMS-T, and CMS-S, can be distinguished for instance using restriction enzyme analysis as well as polymerase chain reaction (PCR) techniques. Traditionally, the pollen-bearing tassel is removed from the inbred designated as the female parent (detasseled) before anthesis (pollen shed) so that the inbred female parent will only be fertilized with pollen from an inbred male parent. One row of the male inbred parents is planted for every four to six rows of the female inbred. However, CMS does not function equally well in all genotypes and is subject to breakdown during adverse weather conditions that could result in the loss of the entire hybrid seed crop.

The GHS method of the present invention eliminates the need for cytoplasmic male sterile (CMS) germplasm and by eliminating the need to maintain this CMS germplasm in a breeding program thereby saving in inventory costs and the costs of maintaining CMS parent lines. The method may also reduce the multiple cultivars needed to use a CMS system, and associated time and effort required to insert transgenes and other desirable genotype traits into a CMS germplasm background. The method of the present invention can be applied to any parent in a breeding program therefore allowing for hybrid seed products that before were difficult to efficiently provide to the corn grower.

Hand and Mechanical Detasseling

The detasseling period is usually the most critical and difficult to manage period in hybrid corn seed production. To achieve the necessary genetic purity standards all tassels from the female parent rows must be removed prior to shedding and/or before silk emergence. This will force cross-pollination between the male and female rows in hybrid production. The detasseling operation involves a physical removal of tassels either manually or in combination with mechanical devices. The detasseling period usually lasts about two weeks but may range from one to five or more weeks. The detasseling period may be prolonged in fields which have delayed and non-uniform germination, variation in soil fertility, waterlogging in early stages, significant pre-flowering water stress, heavy insect infestation resulting in plant stunting, and high incidence of foliar diseases. Often there are a critical few days in which detasseling must be completed to prevent self pollination by the female parent. Tassels must be removed from all female plants before shedding and silk emergence.

Inclement weather is most often the reason that a hybrid corn production crop is lost. A windstorm or heavy rain can lodge and tangle the female parent just as tassels emerge, and make driving or walking through the field difficult. High temperatures can affect both the emergence of silks and tassels as well as the performance of the detasseling crew. Damage to the female parent caused by cutting of the leaves or removal of the leaves with the tassel can cause yield reduction of the hybrid seed and smaller seed size.

Mechanical detasselers mounted on high clearance machines consist of two general types: "Cutters"—a rotating blade or knife operates at various planes from horizontal to vertical, adjustable in height, to cut or shred the top of the corn plant including the tassel and "Pullers"—usually 2 small wheels or rollers, adjustable in height, that rotate in opposite directions and grasp the tassel and upper leaves, pulling them upward in a manner comparable to a hand detasseling operation. Pullers are generally preferred to cutters because they typically inflict less damage to upper leaves resulting in higher seed yields. However, use of pullers may result in more genetic contamination as tassels removed with these devices sometimes end up the leaf canopy where they may shed pollen.

Biotechnological Approaches to Hybridization Systems

Methods are known in the art for assembling and introducing constructs into a cell in such a manner that the nucleic acid molecule for a trait is transcribed into a functional mRNA molecule that is translated and expressed as a protein product. For the practice of the present invention, conventional compositions and methods for preparing and using constructs and host cells are well known to one skilled in the art, see for example, Molecular Cloning: A Laboratory Manual, 3rd edition Volumes 1, 2, and 3 (J. F. Sambrook, D. W. Russell, and N. Irwin, Cold Spring Harbor Laboratory Press, 2000). Methods for making transformation constructs particularly suited to plant transformation include, without limitation, those described in U.S. Pat. Nos. 4,971,908, 4,940,835, 4,769,061 and 4,757,011, all of which are herein incorporated by reference in their entirety. These types of vectors have also been reviewed (Rodriguez, et al. Vectors: A Survey of Molecular Cloning Vectors and Their Uses, Butterworths, Boston, 1988; Glick et al., Methods in Plant Molecular Biology and Biotechnology, CRC Press, Boca Raton, Fla., 1993).

As used herein a "transgenic" organism, or cell, is one whose genome has been altered by the incorporation of foreign genetic material or additional copies of native genetic material, for example by transformation or recombination. The transgenic organism may be a plant, mammal, fungus, bacterium, or virus. As used herein "transgenic plant" means a stably transformed plant or progeny plant of any subsequent generation derived therefrom, wherein the DNA of the plant or progeny thereof contains an introduced exogenous DNA not originally present in a non-transgenic plant of the same strain. The transgenic plant may additionally contain sequences that are native to the plant being transformed, but wherein the exogenous DNA has been altered in order to alter the level or pattern of expression of the gene.

DNA constructs for use in transforming plants typically also comprise other regulatory elements in addition to a promoter, such as but not limited to 3' untranslated regions (such as polyadenylation sites), transit or signal peptides for targeting of a protein or RNA product to a plant organelle, particularly to a chloroplast, leucoplast or other plastid organelle, and marker coding sequence elements. For a description of the use of a chloroplast transit peptide see U.S. Pat. No. 5,188,642, incorporated herein by reference. Promoters are described in U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (coixin promoter), and U.S. Pat. No. 7,151,204 (maize chloroplast aldolase promoter), all of which are incorporated herein by reference.

One skilled in the art would know that various introns, enhancers, transit peptides, targeting signal sequences, 5' and 3' untranslated regions (UTRs) useful in the design of effective plant expression vectors, such as those disclosed, for example, in U.S. Patent Application Publication 2003/01403641 (incorporated herein by reference). Recombinant constructs prepared in accordance with the present invention also generally include a 3' untranslated DNA region (UTR) that typically contains a polyadenylation sequence following the polynucleotide coding region. Examples of useful 3' UTRs include but not limited to those from the nopaline synthase gene of *Agrobacterium tumefaciens* (nos), a gene encoding the small subunit of a ribulose-1,5-bisphosphate carboxylase-oxygenase (rbcS), and the T7 transcript of *Agrobacterium tumefaciens*.

Constructs and vectors may also include a transit peptide for targeting of a protein product, particularly to a chloroplast, leucoplast or other plastid organelle or vacuole or an extracellular location. For descriptions of the use of chloroplast transit peptides, see U.S. Pat. No. 5,188,642 and U.S. Pat. No. 5,728,925, herein incorporated by reference in their entirety. Many chloroplast-localized proteins are expressed from nuclear genes as precursors and are targeted to the chloroplast by a chloroplast transit peptide (CTP). Examples of other such isolated chloroplast proteins include, but are not limited to those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS) and transit peptides described in U.S. Pat.

No. 7,193,133, herein incorporated by reference. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide, such as, the *Arabidopsis thaliana* EPSPS CTP (CTP2, Klee et al., *Mol. Gen. Genet.* 210:437-442), and the *Petunia hybrida* EPSPS CTP (CTP4, della-Cioppa et al., *Proc. Natl. Acad. Sci. USA* 83:6873-6877) has been show to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. No. 5,627,061, U.S. Pat. No. 5,633,435, U.S. Pat. No. 5,312,910, EP 0218571, EP 189707, EP 508909, and EP 924299).

Transformation constructs may permit the integration of the expression unit between the T-DNA (transfer DNA) borders into the genome of a plant cell. The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, LBA4404, EHA101, and EHA105 carrying a plasmid having a transfer function for the expression unit. Other strains known to those skilled in the art of plant transformation can function in the present invention.

The traits of the present invention are introduced into plant cells by transformation methods known to those skilled in the art of plant tissue culture and transformation. Any of the techniques known in the art for introducing expression units into plants may be used in accordance with the invention. Examples of such methods include electroporation as illustrated in U.S. Pat. No. 5,384,253; microprojectile bombardment as illustrated in U.S. Pat. Nos. 5,015,580; 5,550,318; 5,538,880; 6,160,208; 6,399,861; 6,403,865; and 6,946,582; protoplast transformation as illustrated in U.S. Pat. No. 5,508,184; and Agrobacterium-mediated transformation as illustrated in U.S. Pat. Nos. 5,635,055; 5,824,877; 5,591,616; 5,981,840; and 6,384,301. Preferably, corn cells are transformed by the method disclosed in WO9506722 or other methods known in the art of corn transformation and the cells regenerated into fertile plants. Transgenic traits of agronomic importance include, but are not limited to the traits and gene/protein shown in Table 1. DNA compositions of the transgenes of Table 1 are also useful as markers for the presence of the transgene in a plant genome.

TABLE 1

List of transgenic traits and the gene/protein description.

| Trait | Gene/protein | Reference |
|---|---|---|
| Herbicide tolerance | 5-enolpyruvylshikimate-3-phosphate synthases (EPSPS) | U.S. Pat. Nos. 5,627,061, 5,633,435, 6,040,497, 5,094,945, US20060143727, and WO04009761 |
| | glyphosate oxidoreductase (GOX) | U.S. Pat. No. 5,463,175 |
| | glyphosate decarboxylase | WO05003362 and U.S. Patent Publication 20040177399 |
| | glyphosate-N-acetyl transferase (GAT) | U.S. Patent publications 20030083480, 20060200874 |
| | dicamba monooxygenase | U.S. Patent Publications 20030115626, 20030135879 |
| | phosphinothricin acetyltransferase (bar) | U.S. Pat. Nos. 5,646,024, 5,561,236, 5,276,268, 5,637,489, 5,273,894 EP 275,957 |
| | 2,2-dichloropropionic acid dehalogenase | WO9927116 |
| | acetohydroxyacid synthase or acetolactate synthase | U.S. Pat. Nos. 6,225,105, 5,767,366, 4,761,373, 5,633,437, 6,613,963, 5,013,659, 5,141,870, 5,378,824, 5,605,011 |
| | haloarylnitrilase (Bxn) | U.S. Pat. No. 4,810,648 |
| | acetyl-coenzyme A carboxylase | U.S. Pat. No. 6,414,222 |
| | dihydropteroate synthase (sul I) | U.S. Pat. Nos. 5,597,717, 5,633,444, 5,719,046 |
| | 32 kD photosystem II polypeptide (psbA) | Hirschberg et al., 1983, *Science*, 222: 1346-1349 |
| | anthranilate synthase | U.S. Pat. No. 4,581,847 |
| | phytoene desaturase (crtI) | JP06343473 |
| | hydroxy-phenyl pyruvate dioxygenase | U.S. Pat. No. 6,268,549 |
| | protoporphyrinogen oxidase I (protox) | U.S. Pat. No. 5,939,602 |
| | aryloxyalkanoate dioxygenase (AAD-1) | WO05107437 |
| Male/female sterility system | Several | US20050150013 |
| | Glyphosate/EPSPS | U.S. Pat. No. 6,762,344 |
| | Male sterility gene linked to herbicide resistant gene | U.S. Pat. No. 6,646,186 |

TABLE 1-continued

List of transgenic traits and the gene/protein description.

| Trait | Gene/protein | Reference |
|---|---|---|
| | Acetylated toxins/deacetylase | U.S. Pat. No. 6,384,304 |
| | Antisense to an essential gene in pollen formation | U.S. Pat. No. 6,255,564 |
| | DNAase or endonuclease/restorer protein | U.S. Pat. No. 6,046,382 |
| | Ribonuclease/barnase | U.S. Pat. No. 5,633,441 |
| Intrinsic yield | glycolate oxidase or glycolate dehydrogenase, glyoxylate carboligase, tartronic semialdehyde reductase | US2006009598 |
| | eukaryotic initiation Factor 5A; deoxyhypusine synthase | US20050235378 |
| | zinc finger protein | US20060048239 |
| | methionine aminopeptidase | US20060037106 |
| | Several | US20060037106 |
| | 2,4-D dioxygenase | US20060030488 |
| | serine carboxypeptidase | US20060085872 |
| | Several | USRE38,446; 6,716,474; 6,663,906; 6,476,295; 6,441,277; 6,423,828; 6,399,330; 6,372,211; 6,235,971; 6,222,098; 5,716,837; 6,723,897; 6,518,488 |
| Nitrogen use efficiency | fungal nitrate reductases, mutant nitrate reductases lacking post-translational regulation, glutamate synthetase-1, glutamate dehydrogenase, aminotransferases, nitrate transporters (high affinity and low affinities), ammonia transporters and amino acid transporters | US20050044585 |
| | glutamate dehydrogenase | US20060090219 |
| | cytosolic glutamine synthetase; root-specific glutamine synthetase. | EP0722494 |
| | Several | WO05103270 |
| | glutamate 2-oxoglutarate aminotransferase | U.S. Pat. No. 6,864,405 |
| Abiotic Stress tolerance including cold, heat, drought | succinate semialdehyde dehydrogenase | US20060075522 |
| | Several | WO06032708 |
| | Several | US20060008874 |
| | transcription factor | US20060162027 |
| Disease resistance | CYP93C (cytochrome P450) | U.S. Pat. No. 7,038,113 |
| | Several | U.S. Pat. Nos. 7,038,113; 6,653,280; 6,573,361; 6,506,962; 6,316,407; 6,215,048; 5,516,671; 5,773,696; 6,121,436; 6,316,407; 6,506,962; 6,617,496; 6,608,241; 6,015,940; 6,013,864; 5,850,023; 5,304,730); 6,228,992; 5,516,671 |
| Insect resistance | Several | U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; 5,763,241 |

Examples of nucleic acids encoding proteins conferring tolerance to herbicides include 5-enolpyruvylshikimate-3-phosphate synthases (EPSPS; U.S. Pat. No. 5,627,061, U.S. Pat. No. 5,633,435, U.S. Pat. No. 6,040,497, U.S. Pat. No. 5,094,945, WO04074443, and WO04009761), glyphosate oxidoreductase (GOX; U.S. Pat. No. 5,463,175), glyphosate decarboxylase (WO05003362 and U.S. 20040177399), glyphosate-N-acetyl transferase (GAT; U.S. 20030083480) conferring tolerance to glyphosate; dicamba monooxygenase conferring tolerance to auxin-like herbicides such as dicamba (US 20030115626, 20030135879); phosphinothricin acetyl-transferase (bar) conferring tolerance to phosphinothricin or glufosinate (U.S. Pat. No. 5,646,024, U.S. Pat. No. 5,561,236, EP 275,957; U.S. Pat. No. 5,276,268; U.S. Pat. No. 5,637,489; U.S. Pat. No. 5,273,894); 2,2-dichloropropionic acid dehalogenase conferring tolerance to 2,2-dichloropropionic acid (Dalapon) (WO9927116); acetohydroxyacid synthase or acetolactate synthase conferring tolerance to acetolactate synthase inhibitors such as sulfonylurea herbicides (pyrimidinylsuflonylurea herbicides, triazinylsulfonylurea herbicides and thiadiazolylurea herbicides), imidazolinone herbicides, triazolopyrimidine herbicides, pyrimidyloxybenzoate herbicides and phthalide (U.S. Pat. No. 6,225,105; U.S. Pat. No. 5,767,366, U.S. Pat. No. 4,761,373; U.S. Pat. No. 5,633,437; U.S. Pat. No. 6,613,963; U.S. Pat. No. 5,013,659; U.S. Pat. No. 5,141,870; U.S. Pat. No. 5,378,824; U.S. Pat. No. 5,605,011 ); haloarylnitrilase (Bxn) for conferring tolerance to bromoxynil (WO8704181; U.S. Pat. No. 4,810,648; WO8900193); modified acetyl-coenzyme A carboxylase for conferring tolerance to cyclohexanedione (sethoxydim) and aryloxyphenoxypropionate (haloxyfop) (U.S. Pat. No. 6,414,222); dihydropteroate synthase (sul I) for conferring tolerance to sulfonamide herbicides (U.S. Pat. No. 5,597,717; U.S. Pat. No. 5,633,444; U.S. Pat. No. 5,719,046); 32 kD photosystem II polypeptide (psbA) for conferring tolerance to triazine herbicides (Hirschberg et al., 1983, *Science,* 222: 1346-1349); anthranilate synthase for conferring tolerance to 5-methyltryptophan (U.S. Pat. No. 4,581,847); dihydrodipicolinic acid synthase (dapA) for conferring to tolerance to aminoethyl cysteine (WO8911789); phytoene desaturase (crtI) for conferring tolerance to pyridazinone herbicides such as norflurazon (JP06343473); hydroxy-phenyl pyruvate dioxygenase for conferring tolerance to cyclopropylisoxazole herbicides such as isoxaflutole (WO 9638567; U.S. Pat. No. 6,268,549); modified protoporphyrinogen oxidase I (protox) for conferring tolerance to protoporphyrinogen oxidase inhibitors (U.S. Pat. No. 5,939,602); and aryloxyalkanoate dioxygenase (AAD-1) for conferring tolerance to an herbicide containing an aryloxyalkanoate moiety (WO05107437). Examples of such herbicides include phenoxy auxins (such as 2,4-D and dichlorprop), pyridyloxy auxins (such as fluroxypyr and triclopyr), aryloxyphenoxypropionates (AOPP) acetyl- coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac).

Crop plants have been developed for resistance to herbicides based on mutagenesis and selection followed by traditional breeding, corn has been selected to be resistant to cyclohexadinone and imidazolinone herbicides, canola has been selected to be resistant to imidazolinone and triazine herbicides and soybean resistant to sulfonylurea herbicides. These resistant varieties can be combined by traditional breeding with an event produced by biotechnology methods that demonstrate a differential tolerance to glyphosate, such as, male sterility. These combined herbicide tolerance traits are useful in the present invention in a female parent plant of a hybrid seed production system in which the male parent is not tolerant to cyclohexadinone and imidazolinone, imidazolinone and triazine, or sulfonylurea herbicides.

In one embodiment of the present invention, a glyphosate tolerant trait (transgene comprising a glyphosate tolerant modified class I EPSPS, a glyphosate tolerant class II EPSPS, glyphosate tolerant class III EPSPS, or a glyphosate inactivating enzyme) and other traits of agronomic importance (Table 1) are introduced into the germplasm of the female or male parent as required either by direct transformation of an elite inbred parents or by first transforming an easily transformable inbred and then introducing the trait by breeding into the elite inbred parents. The traits present in individual genotypes are then combined to obtain the required traits in a particular female or male parent.

Lines of transgenic glyphosate tolerant crop plants contemplated for use in the methods of the present invention include corn, cotton, soybean, sugarbeet, alfalfa, wheat, among others, that express a gene imparting glyphosate tolerance have been commercialized or are currently in commercial stages of development, for example, Roundup Ready™ alfalfa J-101 and J-163 (WO 04/070020), Roundup Ready™ Cotton 1445 and MON88913 (U.S. Pat. No. 6,740,488, U.S. Pat. No. 7,381,861), Roundup Ready™ corn GA21 and nk603 and MON88017 (U.S. Pat. No. 6,825,400 and U.S. 20080028482), and Roundup Ready™ Sugarbeet (U.S. 20040172669), Roundup Ready™ Canola RT73 (U.S. 20040018518), and Roundup Ready™ Soybean 40-3-2 and MON89788 (U.S. 20060282915). Additional glyphosate tolerant crops under development include wheat MON71800 (U.S. Pat. No. 6,689,880), ASR368 bentgrass (WO 04/053062), and DP356043 soybean (U.S. 20080051288). Production of transgenic lines of other plant species expressing a glyphosate-tolerance gene may be produced by techniques known in the art, see, e.g. U.S. Pat. Nos. 5,312,910; 5,310,667; and 5,463,175.

In another embodiment of the present invention, more than one trait is introduced into an inbred by repeatedly transforming the same inbred with a new trait provided on a transformation construct.

In another embodiment of the present invention, more than one trait is introduced into an inbred by providing more than one trait on a DNA construct used for transformation.

In another embodiment of the present invention, a combination of methods describe above are applied to introduce more than one trait in an inbred.

An "elite inbred" or "elite genotype" is any plant line that has resulted from breeding and selection for superior agronomic performance. Examples of elite corn genotypes suitable for use in the present invention include, but are not limited to those listed in Tables 2 and 3, herein incorporated by reference. The genotypes can be transformed to comprise a glyphosate tolerance transgene or other herbicide tolerance transgenes (Table 1) and events selected for suitability as a female or male parent in a hybrid seed production system of the present invention.

TABLE 2

List of elite corn genotypes.

| U.S. Pat. No. | Line | U.S. Pat. No. | Line | U.S. Pat. No. | Line | U.S. Pat. No. | Line | U.S. Pat. No. | Line |
|---|---|---|---|---|---|---|---|---|---|
| 5,731,492 | PH19A | 5,731,500 | CG5NF22 | 5,633,427 | PHHB | 5,567,861 | PHN46 | 5,489,744 | 4P33339 |
| 5,731,493 | PH63B | 5,731,501 | CG4NU15 | 5,633,428 | LH262 | 5,569,813 | ZS0223 | 5,491,286 | PHKM5 |
| 5,811,645 | NP2045 | 5,750,834 | PH80B | 5,633,429 | LH227 | 5,569,816 | phajo | 5,491,293 | LH225 |
| 5,817,914 | NP993 | 5,750,835 | PH47A | 5,639,941 | LH226 | 5,569,818 | phap8 | 5,491,296 | LH176 |
| 5,824,843 | LH290 | 5,750,847 | PH38D | 5,639,942 | LH235 | 5,569,819 | PHPP8 | 5,495,065 | PHW06 |
| 5,824,848 | F361 | 5,750,849 | PH05W | 5,639,943 | LH234 | 5,569,820 | ZS1284 | 5,495,067 | LH252 |
| 5,824,849 | 171KI3 | 5,750,850 | LH242 | 5,639,946 | PHDP0 | 5,569,821 | PHT11 | 5,495,068 | LH231 |
| 5,824,852 | NP2013 | 5,750,851 | QH101 | 5,675,066 | PH06N | 5,569,822 | phte4 | 5,495,069 | PHTE4 |
| 5,841,015 | PH05G | 5,750,852 | NR109 | 5,684,227 | LH177 | 5,569,826 | ZS0114 | 5,506,367 | PHP38 |
| 5,844,116 | PH1W2 | 5,763,743 | PH63A | 5,689,034 | PH24E | 5,576,473 | 7054 | 5,506,368 | PHN82 |
| 5,844,117 | PHOGP | 5,763,744 | PH67A | 5,708,189 | PHP38 | 5,585,533 | ZS0560 | 5,527,986 | PHTD5 |
| 5,850,007 | PH1MR | 5,763,746 | PH20A | 5,714,671 | ASG06 | 5,585,534 | ZS0853 | 5,530,181 | 899 |
| 5,850,008 | LH263 | 5,763,752 | ZSO1602 | 5,723,721 | CG00685 | 5,585,539 | ZS1791 | 5,530,184 | PHAP1 |
| 5,850,009 | PH0HC | 5,763,753 | ZS01262 | 5,723,722 | PHND1 | 5,585,541 | ZS1513 | 5,534,661 | PHKW3 |
| 5,850,010 | PH56C | 5,763,754 | ZS01219 | 5,723,723 | PH44A | 5,589,606 | ZS1679 | 5,536,900 | CG00653 |
| 5,856,614 | 01IZB2 | 5,763,755 | ZSO1172 | 5,723,724 | ZS01591 | 5,602,314 | ZS1022 | 5,541,518 | PHRD6 |
| 5,859,313 | PHKVO | 5,763,757 | PH07D | 5,723,725 | ZS01101 | 5,602,315 | ZS1202 | 5,543,575 | PHK46 |
| 5,859,316 | PH0HR | 5,763,759 | LH291 | 5,723,726 | ZS01452 | 5,602,316 | ZS1783 | 5,545,809 | PHBG4 |
| 5,859,317 | PH22G | 5,767,339 | 85857 | 5,723,727 | ZS01429 | 5,602,318 | PHDG1 | 5,545,811 | LH189 |
| 5,859,322 | 3ISI2 | 5,767,340 | PHBR2 | 5,723,728 | ZS01819 | 5,608,138 | PHKV1 | 5,545,812 | PHNJ2 |
| 5,859,353 | AR5252bm3 | 5,767,341 | LH228 | 5,723,729 | ZS01250 | 5,608,139 | PHO5F | 5,545,813 | PHRF5 |
| 5,859,354 | PH09B | 5,770,790 | PH41E | 5,723,730 | ZS01595 | 5,608,140 | PH38B | 5,545,814 | PHFR8 |
| 5,859,355 | 17DHD12 | 5,773,683 | LH283 | 5,728,923 | CG3ND97 | 5,618,987 | PH42B | 5,557,034 | PHN18 |
| 5,861,541 | PH10A | 5,777,196 | 01CSI6 | 5,728,924 | NP938(934) | 5,625,129 | PHDD6 | 5,557,987 | PHTP9 |
| 5,866,763 | ZS01220 | 5,777,197 | 3INI2 | 5,731,502 | CG5NA58 | 5,625,131 | ZS0541 | 5,563,320 | PH54B |
| 5,866,767 | PH79A | 5,780,705 | ZS01301 | 5,731,503 | NP948 | 5,625,132 | PH08B | 5,563,321 | PHGF5 |
| 5,866,768 | PHO2T | 5,792,905 | NP982 | 5,731,504 | LH236 | 5,625,133 | PHOC7 | 5,563,322 | PHAG6 |
| 5,880,337 | 4IBZIA | 5,792,906 | NP2034 | 5,731,505 | PH24M | 5,625,134 | ZS1679 | 5,563,324 | PHAP9 |
| 5,880,338 | 7523 | 5,792,911 | PH24M | 5,731,506 | CG00766 | 5,625,135 | LH233 | 5,563,325 | PHBE2 |
| 5,880,339 | SNBK | 5,792,912 | PH00M | 5,750,829 | PHOAA | 5,723,731 | ASG05 | 5,563,327 | ZS0510 |
| 5,880,341 | 91INH2 | 5,792,915 | PHOAV | 5,750,830 | PH15A | 5,723,739 | LH281 | 5,602,317 | PHAAO |
| 5,880,342 | 17DIA1 | 5,811,637 | PH40B | 5,750,831 | PH25A | 5,728,919 | PHBF0 | 5,880,347 | LH273 |
| 5,880,347 | LH264 | 5,811,641 | LH179 | 5,750,832 | PH44G | 5,728,922 | CG5NA01 | 5,880,349 | 7571 |
| 6,127,608 | 7791 | 6,143,961 | RQAA8 | 6,084,160 | PH0CD | 5,977,458 | AR5651bm3 | 5,880,350 | LH237 |
| 6,242,675 | LH293 | 6,143,962 | PH2KN | 6,084,161 | ASG25 | 5,977,459 | LH266 | 5,889,188 | PH0B4 |
| 6,245,975 | LH245 | 6,147,284 | PH2E4 | 6,084,162 | 86ISI15 | 5,977,460 | LH303 | 5,902,922 | FEBS |
| 6,248,941 | 17DHD16 | 6,150,590 | LH267 | 6,084,163 | BE4547 | 5,981,855 | LH301 | 5,905,191 | 8F286 |
| 6,252,146 | 90DHQ2 | 6,153,817 | PH0DH | 6,091,007 | PH21T | 5,986,182 | 4SQ601 | 5,910,625 | 3AZA1 |
| 6,252,147 | LH279 | 6,156,957 | NP991 | 6,096,952 | 01DHD16 | 5,986,184 | PH1TB | 5,910,635 | 91DFA-5 |
| 6,252,148 | LH244 | 6,160,210 | 8982-11-4-2 | 6,096,953 | PH224 | 5,986,185 | PH24D | 5,910,636 | ASG20 |
| 6,259,004 | PH2VE | 6,166,303 | PH1CP | 6,103,958 | ASG26 | 5,986,186 | LH229 | 5,912,420 | ZS03940 |
| 6,265,645 | 8849 | 6,166,304 | NP2208 | 6,103,959 | ASG28 | 5,986,187 | LH277 | 5,912,421 | 91ISI6 |
| 6,281,414 | LH287 | 6,169,230 | 29MIFI2 | 6,107,550 | PH0V0 | 5,990,393 | PH1CN | 5,914,452 | MF1113B |
| 6,291,748 | WDHQ11 | 6,169,231 | RQAB7 | 6,111,171 | 90LCL6 | 5,990,394 | LH261 | 5,917,125 | PH03D |
| 6,303,850 | 09DSS1 | 6,169,233 | NP2211 | 6,111,172 | 22DHD11 | 5,990,395 | W1498A | 5,917,134 | PHDN7 |
| 6,310,274 | PH36E | 6,172,284 | ZS02461 | 6,114,606 | ASG17 | 5,994,631 | WQDS2 | 5,920,003 | 01DIB2 |
| 6,313,381 | PH50P | 6,172,285 | LH198Bt810 | 6,114,609 | AR5253bm3 | 5,998,710 | NL085B | 5,922,935 | 82DHB1 |
| 6,313,382 | PH8V0 | 6,175,063 | 3DHA9 | 6,114,610 | ASG27 | 5,998,711 | PH09E | 5,922,936 | 8M222 |
| 6,313,383 | PH4TV | 6,175,064 | LH200BT810 | 6,114,611 | WDHQ2 | 6,015,944 | LH284 | 5,929,313 | PHMJ2 |
| 6,313,384 | PH2JR | 6,180,858 | LH172Bt810 | 6,114,613 | PH3GR | 6,020,543 | PH1B5 | 5,932,787 | SBB1 |
| 6,316,701 | NP2138 | 6,184,444 | NP2115 | 6,118,051 | PH1NF | 6,025,547 | PH1CA | 5,932,788 | 86ISI3 |
| 6,316,702 | PH4PV | 6,184,445 | PH3P0 | 6,118,053 | PH0JG | 6,031,160 | 7OLDL5 | 5,936,144 | ZS01231 |
| 6,316,703 | PH3DT | 6,184,446 | GSC3 | 6,118,054 | PH189 | 6,031,161 | GM9215 | 5,936,145 | 87DIA4 |
| 6,316,704 | PH5D6 | 6,184,447 | GSC1 | 6,118,056 | PH1EM | 6,034,304 | 90LDC2 | 5,936,146 | 79310J2 |
| 6,320,106 | PH9K0 | 6,187,999 | NP2017 | 6,121,519 | 90DJD28 | 6,034,305 | 90QDD1 | 5,936,148 | PH1GC |
| 6,323,403 | GF6150 | 6,188,001 | PH1W0 | 6,121,520 | PH12C | 6,034,306 | R398D | 5,939,606 | 01DHD10 |
| 6,329,575 | 2227BT | 6,188,002 | 01IZB2 | 6,121,522 | PH55C | 6,037,531 | RDBQ2 | 5,939,607 | PH2CB |
| 6,329,578 | ZS02433 | 6,188,003 | R762 | 6,121,523 | PH3EV | 6,040,507 | HX621 | 5,939,608 | PH080 |
| 6,333,451 | PH0B3 | 6,191,344 | ASG10 | 6,121,525 | ZS4199 | 6,040,507 | HX622 | 5,942,670 | PH14T |
| 6,333,453 | PH2EJ | 6,191,345 | LH253 | 6,124,529 | PH2V7 | 6,040,508 | 01HG12 | 5,942,671 | PH185 |
| 6,340,786 | 17INI30 | 6,194,642 | GSC2 | 6,124,530 | PH4TF | 6,043,416 | HX740 | 5,948,957 | PH19V |
| 6,346,660 | MR724 | 6,201,171 | 86ISI27 | 6,124,531 | PH3KP | 6,043,417 | 79314N1 | 5,952,551 | ZS09247 |
| 6,353,158 | ZS02234 | 6,204,438 | NP2141 | 6,124,532 | PH2MW | 6,043,418 | 17INI20 | 5,952,552 | CRAUGSH2W-89 |
| 6,353,159 | NP2213 | 6,211,446 | 91ISI5 | 6,124,533 | PH2N0 | 6,046,387 | 17DHD7 | 5,962,770 | 91DHA1 |
| 6,353,160 | 4SCQ3 | 6,211,447 | 22DHQ3 | 6,124,534 | PH1K2 | 6,046,388 | 83INI8 | 5,965,798 | LH300 |
| 6,353,161 | 01HF13 | 6,215,050 | 91INI12 | 6,124,535 | PH226 | 6,046,389 | 83InI14 | 5,965,799 | 91ISI4 |
| 6,355,867 | 87ATD2 | 6,222,103 | PH45A | 6,127,609 | PH2VJ | 6,046,390 | 01INL1 | 5,969,212 | 79103A1 |
| 6,355,868 | 1874WS | 6,222,104 | NP948 | 6,127,610 | PH1M8 | 6,049,020 | LH286 | 5,969,220 | ASG22 |
| 6,359,200 | 8M116 | 6,222,105 | 86ISI26 | 6,130,368 | WQCD10 | 6,054,640 | ASG29 | 5,969,221 | 82IUH1 |
| 6,362,403 | FBLL | 6,222,106 | 01IUL6 | 6,130,370 | PH1B8 | 6,060,649 | ASG07 | 5,969,222 | |
| 6,362,404 | 17QFB1 | 6,225,538 | 89ADH11 | 6,133,512 | 17DHD5 | 6,069,303 | QH111 | 5,973,238 | LH302 |
| 6,365,805 | 83DNQ2 | 6,229,075 | R412H | 6,133,513 | PH0WD | 6,072,108 | 09DSQ1 | 5,973,239 | LH265 |
| 6,365,806 | 94INK1A | 6,229,076 | 01HGI4 | 6,133,514 | PH3GK | 6,072,109 | JCRNR113 | 5,977,451 | PHFW4 |
| 6,372,969 | NL054B | 6,232,532 | LH185Bt810 | | | | | | |

TABLE 2-continued

List of elite corn genotypes.

| U.S. Pat. No. | Line | U.S. Pat. No. | Line | U.S. Pat. No. | Line | U.S. Pat. No. | Line | U.S. Pat. No. | Line |
|---|---|---|---|---|---|---|---|---|---|
| 6,380,467 | 6F545 | 6,232,533 | R372H | 6,137,036 | PH2VK | 6,072,110 | NP2029 | 5,977,452 | 01IBH10 |
| 6,384,303 | ZS02338 | 6,232,534 | R660H | 6,137,037 | PH1MD | 6,077,996 | ASG09 | 5,977,453 | 91CSI-1 |
| 6,388,177 | F274 | 6,232,535 | 16IUL2 | 6,137,038 | SM4603 | 6,077,997 | PHOWE | 5,977,455 | WKBC5 |
| 6,388,178 | MBZA | 6,232,536 | F307W | 6,140,562 | PH04G | 6,077,999 | 86AQV2 | 5,977,456 | PH1M7 |
| 6,388,179 | PH4TW | 6,239,334 | F351 | 6,140,563 | NP2151 | 6,080,919 | PH1GG | 6,399,860 | R327H |
| 6,395,967 | FR3351 | 6,812,388 | I244225 | 6,727,413 | PH5DR | 6,506,965 | RPK7346 | 6,407,320 | FR2108 |
| 6,914,177 | PH86T | 6,815,592 | PH3AV | 6,730,833 | LH254 | 6,573,438 | NP2044BT | 6,410,830 | FR3383 |
| 6,927,327 | PHAVN | 6,815,593 | G0302 | 6,730,834 | PH5WB | 6,600,095 | PH8W4 | 6,414,227 | IT302 |
| 6,930,230 | PHB6R | 6,815,594 | G1202 | 6,730,835 | PH7CH | 6,617,500 | M42618 | 6,414,228 | FR3303 |
| 6,933,425 | PH91C | 6,818,811 | PH3PG | 6,730,836 | PH54M | 6,624,345 | MV7100 | 6,420,634 | 9034 |
| 6,933,426 | BE8736 | 6,818,812 | G2202 | 6,730,837 | PH726 | 6,627,800 | 3JP286 | 6,420,635 | G1500 |
| 6,946,590 | MV5125 | 6,822,145 | N16028 | 6,734,348 | PH48V | 6,632,986 | BE4207 | 6,420,636 | FR3311 |
| 6,949,699 | PHCWK | 6,828,492 | G4901 | 6,737,036 | PH3PV | 6,632,987 | CI9805 | 6,420,637 | I389972 |
| 6,956,151 | E24018 | 6,831,216 | LH247 | 6,740,795 | PH77V | 6,635,808 | JCR503 | 6,423,888 | PH77C |
| 6,956,152 | MV8735 | 6,833,499 | KW7648 | 6,740,796 | PH7JB | 6,635,809 | NR401 | 6,426,451 | IT201 |
| 6,956,153 | PHC5H | 6,833,500 | HX894 | 6,740,797 | NP2316 | 6,635,810 | 4VP500 | 6,426,453 | G3000 |
| 6,958,438 | PHACE | 6,835,878 | LH322 | 6,740,798 | PH70R | 6,642,440 | 7SH385 | 6,429,363 | 94INK1B |
| 6,967,267 | PH77P | 6,835,879 | WICY418C | 6,747,194 | RAA1 | 6,642,441 | KW4773 | 6,433,259 | PH3HH |
| 6,967,268 | PHB6V | 6,838,601 | LH289 | 6,747,195 | VMM1 | 6,646,187 | NP2073 | 6,433,260 | 6TR512 |
| 6,967,269 | PH8JR | 6,844,489 | NP2174 | 6,747,196 | PH3RC | 6,646,188 | PSA104 | 6,433,261 | 89AHD12 |
| 6,969,788 | PHBAB | 6,846,976 | PH6WA | 6,753,426 | MNI1 | 6,653,536 | 5XH755 | 6,433,262 | I889291 |
| 6,969,790 | PHB1V | 6,849,790 | G3601 | 6,756,527 | 5750 | 6,653,537 | 1445-008-1 | 6,437,223 | 2070BT |
| 6,972,356 | PH3PR | 6,849,791 | PH6CF | 6,756,528 | PH6KW | 6,657,109 | NP2015 | 6,437,224 | 3323 |
| 6,972,357 | PH8TN | 6,852,914 | HC53 | 6,756,530 | PH951 | 6,660,916 | 7SH383 | 6,441,279 | G1900 |
| 6,974,900 | PH5WA | 6,852,915 | LH283BtMON810 | 6,759,578 | PH6ME | 6,664,451 | LH310 | 6,441,280 | 16IUL6 |
| 6,979,764 | PH58C | 6,855,877 | 85DGD1 | 6,759,579 | NP2171 | 6,670,531 | I880S | 6,444,881 | 7RN401 |
| 6,979,765 | G6103 | 6,855,878 | PH76T | 6,759,580 | PH87H | 6,677,509 | RR728-18 | 6,444,882 | UBB3 |
| 6,984,779 | G1103 | 6,858,786 | I390185 | 6,765,132 | PH26N | 6,683,234 | LH320 | 6,444,883 | 6077 |
| 6,987,218 | KW4U110 | 6,864,409 | WDDQ1 | 6,765,133 | RII1 | 6,686,519 | 11084BM | 6,444,884 | I014738 |
| 6,989,476 | 3633BM | 6,864,410 | N10018 | 6,770,802 | PH9AH | 6,686,520 | W60028 | 6,452,074 | TDC1 |
| 6,989,477 | 5020 | 6,864,411 | PH6MN | 6,774,289 | PH51H | 6,693,231 | PH1GD | 6,452,075 | GF6151 |
| 6,989,478 | PH6HR | 6,872,873 | PH7BW | 6,774,290 | PH94T | 6,693,232 | LH295 | 6,452,076 | 7180 |
| 7,002,063 | BT751-31 | 6,872,874 | PH890 | 6,777,599 | PH7AB | 6,700,041 | PH1BC | 6,455,764 | WQDS7 |
| 7,002,064 | A60059 | 6,878,863 | PH876 | 6,781,042 | PH5FW | 6,706,954 | PH4V6 | 6,459,021 | X532Y |
| 7,009,093 | PH183 | 6,878,864 | PHAPV | 6,781,043 | PH75K | 6,706,955 | NP2276 | 6,459,022 | I465837 |
| 7,012,177 | PH714 | 6,878,865 | PHB5R | 6,784,348 | KW7606 | 6,710,233 | NP2222 | 6,469,232 | 1784S |
| 7,015,386 | PHA9G | 6,881,880 | PH8DB | 6,784,349 | PH8CW | 6,717,036 | Ph0R8 | 6,469,233 | LH176Bt810 |
| 7,022,903 | W69079 | 6,881,881 | PH51K | 6,784,350 | PH8PG | 6,717,037 | PH581 | 6,469,234 | 6RC172 |
| 7,022,904 | PH8BC | 6,884,930 | 4XA321 | 6,797,869 | RBO1 | 6,717,038 | PH6WR | 6,469,235 | 3327 |
| 7,030,302 | PHBBP | 6,888,051 | PH87P | 6,803,509 | 9SM990 | 6,717,039 | PH5HK | 6,476,298 | 7SH382 |
| 7,034,213 | PHAKC | 6,897,361 | PH8KG | 6,806,408 | PH5TG | 6,717,040 | PH5W4 | 6,476,299 | I181664 |
| 7,041,884 | 291B | 6,897,363 | PH4CV | 6,806,409 | I501150 | 6,720,486 | PH0KT | 6,483,014 | NP2010 |
| 7,041,885 | KWU7104 | 6,903,254 | PH705 | 6,806,410 | I390186 | 6,720,487 | PH4GP | 6,483,015 | FR3361 |
| 7,049,498 | 413A | 6,906,250 | LH331 | 6,809,240 | PH6JM | 6,723,900 | PHJ8R | 6,486,386 | 1778S |
| 7,057,100 | W23129 | 6,906,251 | PH5DP | 6,809,243 | KW4636 | 6,723,901 | NP2052 | 6,492,581 | I362697 |
| 7,060,880 | G1704 | 6,909,036 | BX20010 | 6,809,244 | I363128 | 6,723,902 | PH7CP | 6,506,964 | RPK7250 |
| 7,060,880 | G1704 | 6,909,037 | BX20033 | 6,812,386 | LH246 | 6,723,903 | PH6WG | 6,911,588 | 6RT321 |
| RE38,768 | G1900 | 6,909,039 | PH77N | 6,812,387 | 2JK221 | 6,727,412 | PH54H | | |

TABLE 3

List of inbred corn genotypes.

| Application No. | Inbred line |
|---|---|
| US20030093826A1 | CI9805 |
| US20030106086A1 | LH321 |
| US20030154524A1 | HOI002 |
| US20030172416A1 | HOI001 |
| US20030177541A1 | 5750 |
| US20030177543A1 | G0502 |
| US20030177544A1 | G1102 |
| US20040068771A1 | HX879 |
| US20040088767A1 | 6803 |
| US20040088768A1 | 5020 |
| US20040098768A1 | G3001 |
| US20040111770A1 | LH268 |
| US20040111771A1 | LH311 |
| US20040111772A1 | LH306 |
| US20040111773A1 | LH351 |
| US20040111774A1 | LHE323 |
| US20040123352A1 | 402A |
| US20040139491A1 | 366C |
| US20040143866A1 | NP2315 |
| US20040194170A1 | PH0GC |
| US20050015834A1 | SE8505 |
| US20050028236A1 | D201 |
| US20050076402A1 | BE1146BMR |
| US20050114944A1 | PHCAM |
| US20050114945A1 | PHCK5 |
| US20050114951A1 | PHC77 |
| US20050114952A1 | PHCND |
| US20050114953A1 | PHCMV |
| US20050114955A1 | PHB00 |
| US20050114956A1 | PHCER |
| US20050120437A1 | PHCJP |
| US20050120439A1 | PHADA |
| US20050120443A1 | PHB8V |
| US20050125864A1 | 6XN442 |

TABLE 3-continued

List of inbred corn genotypes.

| Application No. | Inbred line |
|---|---|
| US20050125865A1 | 4XP811 |
| US20050125866A1 | PHCCW |
| US20050132433A1 | MN7224 |
| US20050132449A1 | BE9514 |
| US20050138697A1 | PHCA5 |
| US20050144687A1 | PHCPR |
| US20050144688A1 | PHAR1 |
| US20050144689A1 | PHACV |
| US20050144690A1 | PHEHG |
| US20050160487A1 | NP2391 |
| US20050172367A1 | PH8WD |
| US20050177894A1 | D501 |
| US20050177896A1 | D601 |
| US20050177904A1 | D603 |
| US20050223443A1 | PHCEG |
| US20050273876A1 | W16090 |
| US20050273877A1 | M10138 |
| US20050273878A1 | N61060 |
| US20060048243A1 | NP2460 |
| US20060070146A1 | BS112 |
| US20060107393A1 | PHDWA |
| US20060107394A1 | PH8JV |
| US20060107398A1 | PHEWW |
| US20060107399A1 | PHEDR |
| US20060107400A1 | PHE67 |
| US20060107408A1 | PHE72 |
| US20060107410A1 | PHF1J |
| US20060107412A1 | PHE35 |
| US20060107415A1 | PHEHR |
| US20060107416A1 | PHDPP |
| US20060107418A1 | PHEHC |
| US20060107419A1 | PHANF |
| US20060107420A1 | PHC78 |
| US20060107421A1 | PH8T0 |
| US20060107422A1 | PHDRW |
| US20060107423A1 | PHEGV |
| US20060107426A1 | PHEBA |
| US20060112463A1 | PHENE |
| US20060112464A1 | PHEJW |
| US20060112465A1 | PHAPT |
| US20060130188A1 | PHCND |
| US20060130189A1 | PHCEG |
| US20060130190A1 | PHADA |
| US20060143744A1 | PHEED |

Breeding Methods

Descriptions of breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of Crop Improvement," Longman, Inc., NY, 369-399, 1979; Sneep and Hendriksen, "Plant Breeding Perspectives," Wageningen (ed), Center for Agricultural Publishing and Documentation, 1979; Fehr, in: *Soybeans: Improvement, Production and Uses*, 2nd Edition, *Manograph.*, 16:249, 1987; Fehr, "Principles of Variety Development," *Theory and Technique*, (Vol. 1) and *Crop Species Soybean* (Vol. 2), Iowa State Univ., Macmillan Pub. Co., NY, 360-376, 1987).

In general, two distinct breeding stages are used for commercial development of the female and male inbred containing a transgenic trait. The first stage involves evaluating and selecting a superior transgenic event, while the second stage involves integrating the selected transgenic event in a commercial germplasm.

First a transformation construct responsible for a trait is introduced into the genome via a transformation method. Numerous independent transformants (events) are usually generated for each construct. These events are evaluated to select those with desirable level of performance. The event evaluation process is based on several criteria including 1) transgene expression/efficacy of the trait, 2) molecular characterization of the trait, 3) segregation of the trait, 4) agronomics of the developed event, and 5) stability of the transgenic trait expression. Evaluation of large population of independent events and thorough evaluation result in the greater chance of success.

In a preferred embodiment, backcrossing is used to recover the genotype of an elite inbred with an additional transgenic trait. In each backcross generation, plants that contain the transgene are identified and crossed to the elite recurrent parent. Several backcross generations with selection for recurrent parent phenotype are generally used by commercial breeders to recover the genotype of the elite parent with the additional transgenic trait. During backcrossing the transgene is kept in a hemizygous state. Therefore, at the end of the backcrossing, the plants are self- or sib-pollinated to fix the transgene in a homozygous state. The number of backcross generations can be reduced by molecular (or marker) assisted backcrossing (MABC). The MABC method uses molecular markers to identify plants that are most similar to the recurrent parent in each backcross generation. With the use of MABC and appropriate population size, it is possible to identify plants that have recovered over 98 percent of the recurrent parent genome after only two or three backcross generations.

Forward breeding is any breeding method that has the goal of developing a transgenic variety, inbred line, or hybrid that is genotypically different, and superior, to the parents used to develop the improved genotype. When forward breeding a transgenic crop, selection pressure for the efficacy of the transgene is usually applied during each generation of the breeding program. Additionally, it is usually advantageous to fix the transgene in a homozygous state during the breeding process as soon as possible to uncover potential agronomic problems caused by unfavorable transgene x genotype interactions.

After integrating the transgenic traits into commercial germplasm, the final inbreds and hybrids are tested in multiple locations. Testing typically includes yield trials in trait neutral environments as well as typical environments of the target markets. If the new transgenic line has been derived from backcrossing, it is usually tested for equivalency by comparing it to the non-transgenic version in all environments.

Several types of genetic markers are known to those skilled in the art and can be used to expedite breeding programs. These genetic markers may include Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD).

The present invention also provides for the use of genetic markers and breeding methods to produce corn lines useful in the present invention. The present invention also provides a new hybrid seed and plants grown from the seed, the plant and the seed having the genetic traits of the parents. The present invention therefore provides a method to produce a hybrid seed and plant and plant parts isolated thereof, wherein without limitation these include cells, leaves, roots, stalks, seed, endosperm, embryo, ovule and pollen. In a preferred embodiment of the present invention, the plant part is a seed. The invention also includes and provides transformed plant cells, which comprise a nucleic acid molecule of that provide a glyphosate tolerant phenotype useful in a hybrid seed production system.

Genetic Purity Analysis

A genetic purity analysis is particularly important with breeder and foundation seed. The conventional approach to monitoring genetic purity has been through "grow-out" tests. These tests involve planting out a sample of the seed lot in the greenhouse, winter-nursery, and/or summer season field to evaluate plant development in comparison to the varietal description. Disadvantages of this system include time, and the fact that the genetic material may be evaluated in an environment where it is not well adapted resulting in greater difficulties in identifying off-type vs. true-to-type plants. Laboratory techniques are available to conduct purity analysis, such as, molecular marker analysis. These techniques have the advantages of increased precision and speed.

EXAMPLES

Example 1

Transgenic corn plants are produced by transforming a corn plant cell with a DNA construct. The DNA construct comprises a promoter operably linked to a glyphosate tolerance coding sequence. A promoter that provides vegetative and female tissue expression and less expression in pollen producing cells is preferred. For example, DNA virus promoters such as the cauliflower mosaic virus 35S promoter, or figwort mosaic virus promoter or versions of these promoters that contain duplicated enhancer regions provide transgenic plants that can be selected from a population of transgenic plants with the desired level of expression of the glyphosate tolerance coding sequence. Additional promoters can be used in the construct and tested for providing the desired level of glyphosate tolerance in a transgenic corn plant.

A DNA construct is transformed into a corn cell and the cell regenerated into a fertile plant, the DNA construct comprises a cauliflower virus CaMV 35S promoter (U.S. Pat. No. 5,530, 196 and U.S. Pat. No. 5,359,142) operably linked to an intron region from a heat shock 70 protein (Hsp70) gene of *Zea mays* (U.S. Pat. No. 5,424,412), operably linked to a chloroplast transit peptide coding region (for example, the N-terminal chloroplast transit peptide from 5-enolpyruvylshikimate-3-phosphate synthase (EPSPS) from *Arabidopsis thaliana* Klee, 1987, MGG 210: 437-442), operably linked to a coding region of the non-naturally occurring 5-enolpyruvylshikimate-3-phosphate synthase gene (EPSPS) (which confers glyphosate tolerance) from *Agrobacterium* sp strain CP4, using monocot codon usage (USRE39247 and US20060191038), operably linked to a nos terminator region from the nopaline synthase gene from *Agrobacterium tumefaciens* GenBank E01312).

Corn plants transformed with the DNA construct are produced and unique events that have the desired glyphosate tolerance phenotype are selected by treatment with glyphosate a various growth stages and at various rates of glyphosate. Optimal tassel and anther sensitivity to glyphosate can be determined by treatment with an effective dose of glyphosate during corn plant growth and then measuring the pollen shed or anther extrusion. Rapidly maturing corn inbred lines may have early tassel development and glyphosate treatments and rates can be adjusted as needed to produce male sterility in these inbred lines. Transgenic events for the glyphosate hybrid system were designated as event GHS1, GHS2 and GHS3, and selected by various glyphosate treatments to determine the rates and timing of glyphosate that provide the desired level of male sterility as measured by percent anther extrusion. Glyphosate was applied to a field containing the events using the following parameters:

Nozzle: Tee Jet Air Induction (AI) 110015-VS broadcast (green plus green adaptor) spaced on 30" centers GPA: 10-12 gallons per acre (GPA)

PSI: 30-35 pounds per square inch

Speed: 2-2.5 MPH

Nozzle Height: 16-18" above "cup" of the whorl

Useful Conversions:

| | |
|---|---|
| 29.6 ml = 1 oz | 88 ft/min = 1 mile per hour |
| 3785 ml = 1 gallon | 5280 ft = 1 mile |
| 128 oz = 1 gallon | 1 acre = 43560 square feet, 1 hectare = 2.471 acres |

Roundup Ultra®=3 lb acid equivalent (ae)/gal or 32 oz=0.75 lb ae/gal

Roundup WeatherMax®—22 oz/acre=0.75 lb ae/acre

Nozzle calibration: Determine GPM (gallon per minute) output—Select nozzles and set PSI as specified above. Insure screens are all the same style and size. Collect output (30 sec minimum) of every nozzle at engine operating RPM equivalent to field conditions. Replicate 3 times for consistency and replace any nozzle with greater than +5% variation compared to other nozzles. Repeat until all nozzles are consistent.

Tractor speed—Determine sprayer speed in mph at above spray RPM. Measure off known distance (i.e. 100') and measure 3 times for consistency.

Calibration of application equipment—The following formula was used to calculate spray output in GPA: GPA=5940×GPM (per nozzle), MPH×W; wherein W=Nozzle spacing (in inches) for broadcast spraying.

If GPA does not fall in desired spray range, tractor speed may be adjusted.

Modifications can be made to the glyphosate treatment conditions that are known by those in the art of herbicide application and are within the scope of present invention.

Transgenic events GHS1, GHS2, and GHS3 were treated with one or two applications of glyphosate (Roundup WeatherMax®) over the corn development stages V8-V12 (vegetative 8 leaf—vegetative 12 leaf). These development stages also correlate with pollen development in most inbred corn varieties. In this example, the transgenic events are in an LH198 germplasm crossed to LH287. The fertility score is a measure of the percent risk of anther extrusion (AE) observed at the time of silk emergence from the corn ear. The three events and a LH198DMSRR2 control (CMS germplasm with glyphosate tolerance) were treated with six glyphosate treatments (Table 4). The glyphosate treatments are single applications of 0.75 lb ae/ac at V8 stage (Trt 1), 0.75 lb ae/ac at V10 stage (Trt 2) and 0.54 lb ae/ac at V12 stage (Trt 3), and double applications of 0.75 lb ae/ac at V8 followed by 0.54 lb ae/ac at V12 (Trt 4), 0.75 lb ae/ac at V10 followed by 0.54 lb ae/ac at V12 (Trt 5), and 0.75 lb ae/ac at V8 followed by 0.75 lb ae/ac at V10 (Trt 6). The test was set up as a split plot design with 2 row plots and the glyphosate treatments applied in strips over all of the replications. Results are shown in FIG. 1 and Table 4. FIG. 1 illustrates AE % as averaged across all spray treatments across each test plot and event. The data as shown in Table 4 excludes values from one test plot, but demonstrates the same trend as is seen in FIG. 1.

TABLE 4

Percent anther extrusion (AE %) following indicated glyphosate treatment.

| AE (%) | Trt 1 | Trt 2 | Trt 3 | Trt 4 | Trt 5 | Trt 6 |
|---|---|---|---|---|---|---|
| Event GHS-1 | 2.5 | 0.0 | 12.1 | 0.0 | 0.0 | 0.0 |
| Event GHS-2 | 0.4 | 0.0 | 3.0 | 0.0 | 0.0 | 0.0 |
| Event GHS-3 | 5.9 | 0.1 | 3.5 | 0.0 | 0.0 | 0.0 |
| Control | 0.1 | 0.1 | 0.1 | 0.3 | 0.3 | 0.0 |

Thus, from Table 4, the anther extrusion risk (AE%) for events 1-3 and control line LH198DMSRR2_2 was respectively about 2.5, 0.4, 5.9, and 0.1 for treatment 1 ("Trt1"); 0, 0, 0, and 0.1 for Trt2; 12.1, 3.0, 35, and 0.1 for Trt3; 0, 0, 0, and 0.3 for Trt4; 0, 0, 0, and 0.3 for Trt5; and 0, 0, 0, and 0 for Trt6. These results demonstrate that glyphosate induced sterility is effective with Trt 2, Trt 4, Trt 5 and Trt 6 and is as effective as the CMS germplasm in providing male sterility. An effective range includes a single application rate at approximately V8 with about 0.6 lb ae/ac or more of glyphosate, the exact growth stage may vary depending on the inbred genotype development and the glyphosate treatment at various growth stages can be adjusted to compensate for maturity differences among inbred genotypes. Likewise, the effective dose of glyphosate necessary to provide male sterility may vary on the inbred genotype and the rate of treatment can be modified up or down, an effective dose of glyphosate may be 0.54 lb ae/ac or more, or 0.6 lb ae/ac or more, or 0.68 lb ae/ac or more, or about 0.75 lb ae/ac or more of glyphosate. Two applications of glyphosate at the approximately V8 stage to V12 stage at rates from about 0.54 lb ae/ac to about 0.75 lb ae/ac are particularly effective to ensure male sterility of the treated plants.

Example 2

Trait purity and genotype purity is determined by producing hybrid seed by the method of the present invention in which the field is also planted with potentially contaminating traits and genotypes. The hybrid seed production format is a female:male row ratio of 4:1. Event GHS1 and event GHS2 that are in an LH198 germplasm are used as the female parents and will be sterilized with glyphosate, and the male parents are either nk603 Roundup Ready® corn event (U.S. Pat. No. 6,825,400, herein incorporated by reference in its entirety) or MON88017 event (linked glyphosate tolerant and corn rootworm tolerant, WO05059103, herein incorporated by reference). Different transgenic male parents can be used that contain a transgene for glyphosate tolerance and are not susceptible to male sterility by glyphosate treatment at the rates useful to provide male sterility in the female parent. The male plants may additionally contain transgenic traits of agronomic importance (Table 1) or desirable genotypes (Tables 2 and 3). The genotypes of the male parents in this test comprise inbred parents for nk603 that are designated HCL210RR2, HCL301RR2, LH198RR2-2, and LH283RR2-2. The genotypes of the male parents in this test comprise inbred parents for MON88017 that are designated HCL210CCR1, HCL301CCR1, LH198CCR1 and LH283CCR1. The event MON810 (corn borer tolerant, U.S. Pat. No. 6,713,259, herein incorporated by reference) in an LH198 germplasm is hand planted at 1.0 percent and 3.0 percent into the female parent rows or mixed into the female parent seed bags at those concentrations to simulate contamination germplasm. The plots are planted and Glyphosate is applied at V3, V8 and V10 at 0.75 lb ae/ac. This treatment provides weed control and sterility in the hybrid production plots. Good weed control is essential for reducing plant stress and achieving high yield in a hybrid corn seed production system. The number of glyphosate susceptible plants in the female rows is recorded seven days after the V3 glyphosate treatment. The glyphosate treatment is effective in eliminating any contaminating non-glyphosate tolerant plants in the female rows thereby increasing the purity of the hybrid seed product relative to hybrid seed plots not treated with glyphosate.

Hybrid seed is produced by the method of the present invention and assayed for the presence of nk603, MON810, MON88017 and GHS1 or GHS2. The purity of the transgenic traits in the hybrid seed sample are measured by a polymerase chain reaction (PCRTM) method using DNA primer molecules specific for each event or transgene in an approximate thousand kernel sample of each hybrid seed lot. For example, primer molecules of U.S. Pat. Nos. 6,825,400, U.S. Pat. No. 6,713,259 and WO05059103 are useful to determine the trait purity in the hybrid seed for this experiment. Endpoint TaqMan® (Applied Biosystems, Foster City, Calif.) reagents and process is used, PCR cycle times are determined using the TaqMan® Testing Matrix. Primer sets are developed to identify specific transgenes or transgenic events or genotypic markers. For example, the nk603 event can be identified in the sample using primers of SEQ ID NOs: 1, 2 and 6FAM primer SEQ ID NO: 3; MON810 event can be identified using primers of SEQ ID NOs: 4, 5 and 6FAM primer SEQ ID NO: 6; MON88017 can be identified using primers of SEQ ID NOs: 7, 8, 9 and 6FAM primer SEQ ID NO: 10. Primers of SEQ ID NO:3, SEQ ID NO:6, and SEQ ID NO:10 possess a 5' fluorophore (6FAM). The nucleotide sequences of the primers are, for instance, as follows:

```
SEQ ID NO: 1:   5'-ATGAATGACCTCGAGTAAGCTTGTTAA-3'
SEQ ID NO: 2:   5'-AAGAGATAACAGGATCCACTCAAACACT-3'
SEQ ID NO: 3:   5'-TGGTACCACGCGACACACTTCCACTC-3'
SEQ ID NO: 4:   5'-AGCCACCACTTCTCCTTGGA-3'
SEQ ID NO: 5:   5'-AGGCTACCGAAAGTCCTCGTT-3'
SEQ ID NO: 6:   5'-ATCGATGTGGGCTGCACCGACCT-3'
SEQ ID NO: 7:   5'-GCTTGATGGGGATCAGATTGTC-3'
SEQ ID NO: 8:   5'-CGTTTCCCGCCTTCAGT-3'
SEQ ID NO: 9:   5'-GCAGTATGCCGGAGTTGAC-3'
SEQ ID NO: 10:  5'-CATCCAAACCCGACTCT-3'
```

Other primer molecules can be selected by those skilled in the art from DNA sequences disclosed in U.S. Pat. Nos. 6,825,400, and 6,713,259, and WO05059103, herein incorporated by reference in their entirety.

The results of the analysis are shown in Table 5. A high level of trait and genotype purity is obtained in the hybrid seed product by using the GHS hybrid corn seed production method of the present invention relative to the CMS system (treatments 9 and 10). A sample of about 1080 seeds from each of 10 treatments are assayed for the presence of the female parent event (GHS1, column 3 or GHS2, column 4; NT=not tested) and the male glyphosate tolerant parent (nk603 or MON88017) and for the presence of a contaminating event MON810 that is the variable in the treatments when added at 1 percent or 3 percent to simulate a contaminate in the hybrid seed production field. As shown in Table 5, in treatments 1, 2, 3, and 4 the female parent genotype (GHS1 or GHS2) purity ranges from 99.0 to 100 percent with an average of 99.5 percent and the percent male parent genotype (nk603) purity ranges from 99.1 to 99.8 with an average of 99.5 percent. The percent genotype purity for the CMS system with nk603 as the male parent (treatments 9 and 10) showed that the male parent purity in the hybrid seed ranged from 98 to 98.9 percent with an average of 98.5 percent, thus the GHS hybrid seed production method provides a 1 percent increase in trait purity. Trait purity is especially important for herbicide tolerant traits, any hybrid plant grown from the F1 hybrid seed not having the herbicide tolerant trait will be eliminated when the production field is treated with the herbicide for weed control. The GHS system provides for a high level of herbicide tolerance trait purity in the hybrid seed product. MON88017 comprises a glyphosate tolerance gene and is detected at an average of 0.3 percent (column 6 of Table 5). Treatments 5, 6, 7 and 8 use MON88017 as the male parent, in these treatments the resulting hybrid seed is greater than 99.9 percent pure for the MON88017 parent and greater than 99.5 percent pure for the female GHS parents (GHS1 and GHS2). There is less than 0.2 percent incidence of MON810 relative to the average of 3.5 percent for the CMS hybrid seed method of treatments 9 and 10. The GHS hybrid production method is useful to enhance trait and genotype purity that can result in enhanced performance of the hybrid seed product when grown in a production field.

TABLE 5

Trait purity.

| Treatments | Number of Seeds Tested | Percent of seed positive for GHS1 | Percent of seed positive for GHS2 | Percent of seed positive for NK603 | Percent of seed positive for MON88017 | Percent of seed positive for MON810 |
|---|---|---|---|---|---|---|
| 1 GHS1, NK603 1% MON810 | 1078 | 99.3 | NT | 99.8 | 0.1 | 0.0 |
| 2 GHS2, NK603 1% MON810 | 1079 | NT | 100.0 | 99.1 | 0.7 | 0.1 |
| 3 GHS1, NK603 3% MON810 | 1080 | 99.0 | NT | 99.5 | 0.4 | 0.0 |
| 4 GHS2, NK603 3% MON810 | 1079 | NT | 99.9 | 99.6 | 0.1 | 0.0 |
| 5 GHS1, M88017 1% MON810 | 1080 | 99.2 | NT | 0.3 | 99.9 | 0.1 |
| 6 GHS2, M88017 1% MON810 | 1080 | NT | 99.4 | 0.0 | 99.9 | 0.2 |
| 7 GHS1, M88017 3% MON810 | 1079 | 99.6 | NT | 0.1 | 99.9 | 0.3 |
| 8 GHS2, M88017 3% MON810 | 1080 | NT | 100.0 | 0.1 | 100.0 | 0.1 |
| 9 CMS, NK603 1% MON810 | 1077 | 0.0 | 0.1 | 98.9 | 0.4 | 1.9 |
| 10 CMS, NK603 3% MON810 | 1077 | 0.0 | 0.0 | 98.0 | 0.0 | 5.3 | product. A container (for example, a seed bag) of hybrid seed produced by this method is easily identifiable from a sample the seed because of the greater than 98 percent, or greater than 99 percent transgenic trait or genotype purity of the seed and the presence of the male and female herbicide tolerance genes. Additionally, seed from these treatments is assayed for the presence of MON88017 and MON810. MON810 is not glyphosate tolerant and is planted in the hybrid seed production field to simulate an impurity in the inbred seed population. For treatments 1, 2, 3, and 4, only treatment 2 shows 0.1 percent incidence of MON810 (column 7 of Table 5) compared to treatments 9 and 10 that shows 1.9 percent and 5.3 percent, respectively. This result demonstrates that the GHS hybrid seed production reduces the incidence of contaminating germplasm that could affect yield or trait performance of Yield of a corn plant produced from hybrid seed is affected by the hybrid purity of the seed. A corn crop grown from hybrid seed that contains greater than two percent contaminating parent seed will yield less than a corn crop grown from hybrid seed of greater hybrid purity. This yield differential can be substantial when calculated over the greater than ninety million acres of corn plant in the United States each year. The transgenic trait purity is associated with genotype of the parent in which the transgene has been inserted into its genome, by measuring the trait purity in the hybrid seed sample the genotype purity is also determined.

Example 3

The yield of hybrid seed is important for maintaining profitability in hybrid seed production systems. Surprisingly, we discovered that the hybrid seed yield is increased using the glyphosate hybridization system relative to the CMS system. GHS1 and GHS2 are used as the female parent in a hybrid seed production field with MON88017 or nk603 as the male parent. The GHS fields were treated with glyphosate (V8 and V10 at 22 oz/ac) and the seed harvested from the female rows. Table 6 shows data collected from the test in which GHS1 or GHS2 is pollinated with a male parent, MON88017 or nk603. The average yield is 29.72 kilograms (kg) and 33.39 kg, respectively compared to the CMS-nk603 yield of 29.05 kg.

TABLE 6

Yield of the hybrid seed.

| Event | Total wt (KG) | Average Wt (kg) |
|---|---|---|
| GHS1, MON88017 | 25.9 | 29.72 |
| GHS1, MON88017 | 31.5 | glyphosate |
| GHS1, NK603 | 32.16 | treated |
| GHS1, NK603 | 29.35 | V8-V10 |
| GHS2, MON88017 | 27.5 | 33.39 |
| GHS2, MON88017 | 35.74 | glyphosate |
| GHS2, NK603 | 38.67 | treated |
| GHS2, NK603 | 31.66 | V8-V10 |
| CMS, NK603 | 36.11 | 29.05 |
| CMS, NK603 | 22 | Not glyphosate treated |

Example 4

This example describes a method for the production of hybrid corn seed in which at least one of the parents is not an inbred parent. This multi-cross hybrid production system uses glyphosate and selected transgenic events that have the desired level of performance of glyphosate tolerance. In this system, a single cross female is used that is a cross of two inbred parents, in which at least one of the parents contains a glyphosate tolerance gene and is selected for a glyphosate tolerance phenotype that is vegetative tolerant, female tolerant, and male sterile after treatment with glyphosate. If both parents are homozygous for the glyphosate tolerance gene and phenotype, then the single cross hybrid would be homozygous and by using this hybrid as the female parent in a hybrid seed production system it would perform as if it was a single inbred female parent. If just one parent of the hybrid has the glyphosate tolerance phenotype, then the resulting single hybrid would be hemizygous and vegetatively tolerant and female tolerant to glyphosate and the pollen could be sterilized with the optimized applications of glyphosate.

The glyphosate tolerance phenotype (vegetative tolerance, female tolerant, male sterile) can also be used to make more complex hybrid crosses such as three-way and four-way crosses. In this method, the female parent is a single cross hybrid between 2 inbred parents. A single cross female hybrid parent used in a multi-cross hybrid production system results in increased yields in the hybrid seed production field as a result of the heterosis of the single cross female hybrid parent.

In a multi-cross hybrid production system, the single cross female hybrid parent needs to be created to have the glyphosate tolerance phenotype. To create this hybrid, the female parent should have the glyphosate tolerance phenotype (vegetative tolerant, female tolerant, male sterile) and glyphosate treatment is used in a hybrid production system to make this female parent male sterile. The male parent needs to be protected from glyphosate treatment. The male parent could contain the glyphosate tolerance phenotype (vegetative tolerance, female tolerant, male sterile) and other transgenic traits of agronomic importance, except full glyphosate tolerance or the male could be nontransgenic. The male plant pollinates the female parent and produces the hybrid seed that will be used as the single cross female in subsequence crosses.

The use of the single cross female hybrid parent would proceed in the hybrid seed production system as if it was a single inbred parent. In the hybrid seed production system, the male parent would be fully glyphosate tolerant and the single cross female hybrid parent would be male sterilized with late applications of glyphosate. The resulting hybrid seed would be fully glyphosate tolerant. This system would be particularly useful in hybrid seed production areas that often use single cross females, the females are often tall and difficult to hand or mechanically detassel. This system would eliminate the need for this detasselling operation.

Example 5

A conventional hybrid seed production system comprises male and female parent plants that are arranged such that the hybrid seed can be harvested from the female parent without harvesting seed from the male parents. This is usually performed by separating the male and female parents into rows or blocks. The rows or blocks containing the male parent plants can then be destroyed or removed after pollination has occurred. It would be advantageous to hybrid seed production system if the male and female plants could be interspersed in the field in optimal pollinating proximity for the crop. The area of the field devoted to the male parent could be reduced or pollination efficiency, measured as the amount of hybrid seed produced per unit area, could be increased. Substantial cost savings can be realized by reducing the amount of land required to produce hybrid seed. The ratio of female parent plants to male parent plants can be optimized to reduce the amount of land required to produce the hybrid seed or to provide a high yield of hybrid seed.

The present invention provides a hybrid seed production system in which the optimal ratio of parent plants can be achieved that provides the best use of the land available for producing the hybrid seed or the highest yield or purity of the hybrid seed. In this method, a hybrid seed production system comprises growing a first plant and a second plant in pollination proximity in a field, wherein the first plant (herein referred to as the female parent) is capable of tolerating a first herbicide in the vegetative tissue and female reproductive tissue but not in the male reproductive tissue, and is capable of tolerating a second herbicide, and further wherein the second plant (herein referred to as the male parent) is capable of tolerating the first herbicide, and is sensitive to the second herbicide and treating the first and second plants, prior to pollination, with an effective amount of the first herbicide to render the first plant male sterile while allowing pollen from the second plant to pollinate the first plant; and treating the first and second plants, post pollination, with an effective amount of the second herbicide to halt the further development of the second plant; and harvesting seeds from the first plant.

In this method, the first herbicide is a systemically translocated herbicide that, for example, includes, but not limited to glyphosate, an imidazolinone herbicide, a sulfonylurea herbicide, a sulfonamide herbicide, an aryloxyphenoxypropionate herbicide, or a cyclohexanedione herbicide. The female parent plant has been selected from a population of plants that is vegetatively and female reproductively tolerant to one or more of these systemically translocated herbicides and is male sterile when treated with the herbicide at an appropriate growth and development stage prior to pollen maturation or shed, for example as described in Example 1. The female plant could be a product of genetic engineering and contain a transgene that provides differential tissue expression of a herbicide tolerance protein, for example, a glyphosate tolerant 5-enolpyruvylshikimate-3-phosphate synthase, an imidazolinone herbicide, sulfonylurea herbicide, or sulfonamide herbicide tolerant acetolactate synthase (ALS or AHAS), or an aryloxyphenoxypropionate herbicide or cyclohexanedione herbicide tolerant acetyl-coenzyme A carboxylase (ACCase). The female parent plant could be a selection from mutagen treated plant cells, seeds or plants that have the desired level of male tissue sensitivity to one of the herbicides. The female additionally is tolerant to a second herbicide different from the first herbicide. Table 7 includes, but is not limited to the herbicide tolerance traits described for parents useful in a hybrid seed production system of the present invention. In this description, a corn female parent is a GHS event and tolerant to an ALS/AHAS inhibitor or an ACCase inhibitor or a combination thereof and the male parent is nk603 or MON88017 or GA21 or another corn plant vegetatively and reproductively tolerant to glyphosate; a soybean female parent is a GHS event and tolerant to dicamba, ALS/AHAS inhibitor, 2,4-D, glufosinate or a combination thereof and the male parent is MON89788 or 40-3-2 or another soybean plant vegetatively and reproductively tolerant to glyphosate; a cotton female parent is a GHS event (1445) and is glufosinate, dicamba, 2,4-D, or ALS inhibitor tolerant or a combination thereof and the male parent is MON88913 or another cotton plant vegetatively and reproductively tolerant to glyphosate; a canola female parent is a GHS event and is dicamba, glufosinate, 2,4-D or ALS inhibitor tolerant or a combination thereof and the male parent is RT73 or another canola plant vegetatively and reproductively tolerant to glyphosate; a wheat female parent is a GHS event and is ALS inhibitor or ACCase inhibitor tolerant and the male is MON71800 another wheat plant vegetatively and reproductively tolerant to glyphosate; a rice female parent is a GHS event and ALS inhibitor or ACCase inhibitor tolerant and the male is another rice plant vegetatively and reproductively tolerant to glyphosate.

When the first herbicide is glyphosate, the second herbicide is selected from the group consisting of dinitroaniline herbicide, trifluralin, pendimethalin, ethalfluralin, triazolopyrimidines, chloracetamide, metolachlor, acetochor, dimethenamid-P, alachlor, thiocarbamate, triallate, EPTC, cycloate, benzolfuran, ethofumesate, pyrazolium, difenzoquat-methyl sulfate, a uracil, a phenylurea, a triketone, mesotrione, an isoxazole, isoxaflutole, an acetanilide, an oxadiazole, a triazinone, a sulfonanilide, an amide, an anilide, propanil, a flurochloridone, a norflurazon, a triazine, atrazine, a triazolinone type herbicide, metribuzin, flucarbazone-Na, propoxycarbazone-Na, glufosinate, asulam, bentazon, bialaphos, bromacil, sethoxydim, cyclohexanedione, tralkoxydim, clethodim, sethoxydim, phenylpyrazolin, pinoxaden, dicamba, fosamine, flupoxam, 2-phenoxypropionate, aryloxy-phenoxypropionate, clodinafop-propargyl, fenoxaprop-P-ethyl, diclofop-methyl, fluazifop-P-butyl, quizalofop, picloram, fluormetron, butafenacil, metribuzin, chlorimuron, chlorsulfuron, triasulfuron, mesosulfuron-methyl, foramsulfuron, sulfosulfuron, flumetsulam, halosulfuron, sulfometron, imazamethabenz-methyl, imazaquin, imazethapyr, isoxaben, imazamox, metosulam, pyrithrobac, rimsulfuron, bensulfuron, nicosulfuron, fomesafen, fluroglycofen, KIEI9201, ET751, carfentrazone, mesotrione, sulcotrione, bypyridilium, paraquat, diquat, bromoxynil and fenoxaprop.

When the first herbicide is not glyphosate, for example, an imidazolinone herbicide, a sulfonylurea herbicide, a sulfonamide herbicide, an aryloxyphenoxypropionate herbicide, or a cyclohexanedione herbicide, then the second herbicide can include glyphosate or another herbicide different from the first herbicide.

The female parent and male parent plants are planted in a field in pollinating proximity at a ratio that saves field space or provides optimal hybrid seed production. When a female and male of the present invention are planted in the same row, a ratio of from 1 female to 1 male plant, 2 females to 1 male, 3 females to 1 male, 4 females to 1 male, 5 females to 1 male, 6 females to 1 male, 7 females to 1 male or 8 females to 1 male or more can be selected to optimize the field space or hybrid seed production.

Alternatively, the female and male parent plants can be planted in a field in pollinating proximity, each in a row that saves field space or provides optimal hybrid seed production. The male rows can be treated with a herbicide for which the female is tolerant without damaging the female plants due to spray drift of the herbicide. When a female and male of the present invention are planted in separate rows, a ratio of from 1 female to 1 male plant row, 2 females to 1 male row, 3 females to 1 male row, 4 females to 1 male row, 5 females to 1 male row, 6 females to 1 male row, 7 females to 1 male row or 8 females to 1 male row or more can be selected to optimize the field space or hybrid seed production.

TABLE 7

Herbicide tolerance traits in the parents of the hybrid seed system.

| Female Parent | Male parent |
| --- | --- |
| Corn GHS event, ALS inhibitor tolerant or ACCase inhibitor tolerant | nk603, GA21, MON88017 |
| Soybean GHS event, dicamba tolerant, or ALS inhibitor tolerant, or glufosinate tolerant or 2,4-D tolerant | MON89788, 40-3-2 |
| Cotton GHS event, dicamba tolerant, or ALS inhibitor tolerant, or glufosinate tolerant or 2,4-D tolerant | MON88913 |
| Canola GHS event, dicamba tolerant, or ALS inhibitor tolerant, or glufosinate tolerant or 2,4-D tolerant | RT73 |
| Wheat GHS event, ALS inhibitor tolerant or ACCase inhibitor tolerant | MON71800 |
| Rice GHS event, ALS inhibitor tolerant or ACCase inhibitor tolerant | Glyphosate tolerant |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All references cited herein are incorporated by reference in their entirety.

What is claimed is:

1. A method for producing hybrid corn seed that enhances transgene trait purity and genotype purity comprising:
   (a) planting in a hybrid corn seed production field in pollinating proximity, seeds of a first parent corn plant and a second parent corn plant;
   (b) allowing said seeds to germinate and grow into plants, wherein said first parent corn plant comprises a first glyphosate tolerance transgene and is homozygous for said first glyphosate tolerance transgene and said second parent corn plant comprises a second glyphosate tolerance transgene and is homozygous for said second glyphosate tolerance transgene;
   (c) treating said plants in said seed production field with glyphosate, wherein said treatment consists of:
   two applications of glyphosate of about 0.54-0.75 lb ae/ac at about the V8-V12 growth stages, wherein the amount of glyphosate in the first of said two applications is greater than the amount in the second application;
   and wherein said first parent corn plant is vegetatively and female reproductively tolerant to said glyphosate treatment and rendered male-sterile by said glyphosate treatment, and wherein said second parent corn plant is vegetatively, female, and male reproductively tolerant to said glyphosate treatment;
   (d) allowing the second corn parent plants to pollinate the first parent corn plants in said production field;
   (e) harvesting a hybrid corn seed produced on the first parent corn plant in said production field,
   wherein, the transgene trait purity and genotype purity of said hybrid seed produced by said hybrid seed production method is greater than in a hybrid seed production field not using said hybrid seed production method.

2. The method of claim 1, wherein step (c) comprises
   (c) treating said plants in said seed production field with glyphosate, wherein said treatment consists of:
      (i) about 0.75 lb ae/ac or more applied at the V8 stage followed by about 0.54 lb ae/ac or more applied at the V12 growth stage; or
      (ii) about 0.75 lb ae/ac or more applied at the V10 stage followed by about 0.54 lb ae/ac or more applied at the V12 growth stage;
   and wherein said first parent corn plant is vegetatively and female reproductively tolerant to said glyphosate treatment and rendered male-sterile by said glyphosate treatment, and wherein said second parent corn plant is vegetatively, female, and male reproductively tolerant to said glyphosate treatment.

3. The method of claim 1, wherein a sample of said seed is assayed with a first molecular marker specific for the first glyphosate tolerance transgene or genotype and a second molecular marker specific for the second glyphosate tolerance transgene or genotype.

4. A method for reducing the cost of corn hybrid seed production comprising:
  (a) planting in a hybrid corn seed production field in pollinating proximity, seeds of a first parent corn plant and a second parent corn plant;
  (b) allowing said seeds to germinate and grow into plants, wherein said first parent corn plant comprises a first glyphosate tolerance transgene and is homozygous for said first glyphosate tolerance transgene and said second parent corn plant comprises a second glyphosate tolerance transgene and is homozygous for said second glyphosate tolerance transgene;
  (c) treating said plants in said seed production field with at least two treatments of glyphosate, wherein said treatments consist of: two applications of glyphosate of about 0.54-0.75 lb ae/ac at about the V8-V12 growth stages, wherein the amount of glyphosate in the first of said two applications is greater than the amount in the second application;
  and wherein said first parent corn plant is vegetatively and female reproductively tolerant to said glyphosate treatment and rendered male-sterile by said glyphosate treatment, and wherein said second parent corn plant is vegetatively, female, and male reproductively tolerant to said glyphosate treatment; wherein said plants are not mechanically detasseled or hand detasseled and labor costs are reduced relative to labor costs in a hybrid seed production field not using said method of hybrid corn seed production.
  (d) allowing the second corn parent plants to pollinate the first parent corn plants in said production field;
  (e) harvesting a hybrid corn seed produced on the first parent corn plant in said production field.

5. The method of claim 4, wherein step (c) comprises
  (c) treating said plants in said seed production field with glyphosate, wherein said treatment consists of:
  about 0.75 lb ae/ac or more applied at the V8 stage followed by about 0.54 lb ae/ac or more applied at the V12 growth stage;
    and wherein said second parent corn plant is vegetatively, female and male reproductively tolerant to said glyphosate treatment; wherein said plants are not mechanically detasseled or hand detasseled and the labor costs are reduced relative to labor costs in a hybrid seed production field not using said method of hybrid corn seed production.

6. The method of claim 4, wherein costs of a non-glyphosate herbicide are reduced relative to a hybrid seed production field not using said method of hybrid corn seed production.

7. The method of claim 4, wherein there is a reduced cost due to reduced risk of injury to production workers relative to a hybrid seed production field not using said hybrid seed production method.

8. The method of claim 4, wherein fuel costs are reduced relative to a hybrid seed production field not using said hybrid seed production method.

9. The method of claim 4, wherein cost of fungicide application is reduced relative to a hybrid seed production field not using said hybrid seed production method.

10. The method of claim 4, wherein the second parent is not a cytoplasmic male sterile genotype.

11. The method of claim 4, wherein the cost of equipment is reduced.

12. A method to enhance corn hybrid seed yield comprising:
  (a) planting in a hybrid corn seed production field in pollinating proximity, seeds of a first parent corn plant and a second parent corn plant, wherein said second parent is of a genotype different from the first parent;
  (b) allowing said seeds to germinate and grow into plants, wherein said first parent corn plant comprises a first glyphosate tolerance transgene and is homozygous for said first glyphosate tolerance transgene and said second parent corn plant comprises a second glyphosate tolerance transgene and is homozygous for said second glyphosate tolerance transgene;
  (c) treating said plants in said seed production field with glyphosate, wherein said treatment consists of:
    two applications of glyphosate of about 0.54-0.75 lb ae/ac at about the V8-V12 growth stages, wherein the amount of glyphosate in the first of said two applications is greater than the amount in the second application;
    and wherein said first parent corn plant is vegetatively and female reproductively tolerant to said glyphosate treatment and rendered male-sterile by said glyphosate treatment, and wherein said second parent corn plant is vegetatively, female, and male reproductively tolerant to said glyphosate treatment,
  (d) allowing the second corn parent plants to pollinate the first parent corn plants in said production field;
  (e) harvesting a hybrid corn seed produced on the first parent corn plant in said production field;
  wherein, the corn hybrid seed yield of the corn seed production field is enhanced relative to the corn hybrid seed yield of a corn seed production field comprising the same parental genotypes but not produced by the present method.

13. The method of claim 12, wherein step (c) comprises:
  (c) treating said plants in said seed production field with glyphosate, wherein said treatment consists of:
    (i) about 0.75 lb ae/ac or more applied at the V8 stage followed by about 0.54 lb ae/ac or more applied at the V12 growth stage; or
    (ii) about 0.75 lb ae/ac or more applied at the V10 stage followed by about 0.54 lb ae/ac or more applied at the V12 growth stage;
    and wherein said second parent corn plant is vegetatively, female and male reproductively tolerant to said glyphosate treatment; wherein said plants are not mechanically detasseled or hand detasseled and the labor costs are reduced relative to labor costs in a hybrid seed production field not using said method of hybrid corn seed production.

14. The method of claim 12, wherein the genotypes are selected from Table 2 or Table 3.

15. A corn hybrid seed multi-cross production system that enhances transgene trait purity and genotype purity comprising:
  (a) planting in a hybrid corn seed production field in pollinating proximity, seeds of a first parent corn plant that is a homozygous inbred or a hybrid and a second parent corn plant is a hybrid or open pollinated variety;
  (b) allowing said seeds to germinate and grow into plants, wherein said first parent corn plant comprises a first glyphosate tolerance transgene and said second parent corn plant comprises a second glyphosate tolerance transgene;
  (c) treating said plants in said seed production field with glyphosate, wherein said treatment consists of: two applications of glyphosate of about 0.54-0.75 lb ae/ac at about the V8-V12 growth stages;
  and wherein said first parent corn plant is vegetatively and female reproductively tolerant to said glyphosate treatment and rendered male-sterile by said glyphosate treatment, and wherein said second parent corn plant is vegetatively, female, and male reproductively tolerant to said glyphosate treatment;

(d) allowing the second corn parent plants to pollinate the first parent corn plants in said production field;

(e) harvesting a hybrid corn seed produced on the first parent corn plant in said production field;

wherein, the transgene trait purity and genotype purity of said hybrid seed produced by said hybrid seed production method is greater than in a hybrid seed production field not using said hybrid seed production method.

16. The method of claim 15, wherein step (c) comprises:

(c) treating said plants in said seed production field with glyphosate, wherein said treatment consists of:

(i) about 0.75 lb ae/ac or more applied at the V8 stage followed by about 0.54 lb ae/ac or more applied at the V12 growth stage; or (ii) about 0.75 lb ae/ac or more applied at the V10 stage followed by about 0.54 lb ae/ac or more applied at the V12 growth stage;

and wherein said second parent corn plant is vegetatively, female and male reproductively tolerant to said glyphosate treatment; wherein said plants are not mechanically detasseled or hand detasseled and the labor costs are reduced relative to labor costs in a hybrid seed production field not using said method of hybrid corn seed production.

17. The method of claim 15 comprising assaying a sample of the hybrid seed with a first molecular marker specific for the first glyphosate tolerance transgene or first parent genotype and a second molecular marker specific for the second glyphosate tolerance transgene or second parent genotype, wherein the transgene trait purity and genotype purity of said hybrid seed produced by said hybrid seed production method is greater than in a hybrid seed production field not using said hybrid seed production method.

* * * * *